(12) United States Patent
Hossain et al.

(10) Patent No.: US 11,808,747 B1
(45) Date of Patent: Nov. 7, 2023

(54) HYDROGEN GAS SENSOR, AND METHOD OF MAKING AND USING THEREOF

(71) Applicant: KING FAHD UNIVERSITY OF PETROLEUM AND MINERALS, Dhahran (SA)

(72) Inventors: Mohammad Kamal Hossain, Dhahran (SA); Qasem Ahmed Drmosh, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 2 days.

(21) Appl. No.: 17/858,515

(22) Filed: Jul. 6, 2022

(51) Int. Cl.
    *G01N 33/00*    (2006.01)
    *C23C 14/34*    (2006.01)
    *B82Y 15/00*    (2011.01)

(52) U.S. Cl.
    CPC ........... *G01N 33/005* (2013.01); *C23C 14/34* (2013.01); *B82Y 15/00* (2013.01)

(58) Field of Classification Search
    CPC ....... B82Y 15/00; C23C 14/34; G01N 33/005
    USPC ......................................................... 73/31.05
    See application file for complete search history.

(56) References Cited

U.S. PATENT DOCUMENTS

| | | | |
|---|---|---|---|
| 8,052,898 B2 | 11/2011 | Takano et al. | |
| 2005/0224360 A1* | 10/2005 | Varghese | C25D 11/26 205/171 |
| 2009/0198117 A1* | 8/2009 | Cooper | A61B 5/6846 600/347 |

FOREIGN PATENT DOCUMENTS

| | | | |
|---|---|---|---|
| EP | 2 010 894 B1 | 4/2012 | |
| JP | 2016510405 A | * 7/2016 | |
| KR | 10-0948893 B1 | 3/2010 | |
| KR | 10-2017-0086786 A | 7/2017 | |
| KR | 1766114 B1 | * 8/2017 | ............. G01N 27/12 |

OTHER PUBLICATIONS

Translation of KR-1766114-B1 (Year: 2017).*
Translation of JP-2016510405-A (Year: 2016).*
Paola Zuppella, et al., "Palladium on Plastic Substrates for Plasmonic Devices", SENSORS, vol. 15, Jan. 9, 2015, pp. 1138-1147.
Su Hui Lim, et al., "Flexible Palladium-Based $H_2$ Sensor with Fast Response and Low Leakage Detection by Nanoimprint Lithography", ACS Applied Materials & Interfaces, vol. 5, Jul. 2, 2013, pp. 7274-7281.

(Continued)

*Primary Examiner* — Nathaniel T Woodward
(74) *Attorney, Agent, or Firm* — Oblon, McClelland, Maier & Neustadt, L.L.P.

(57) ABSTRACT

A hydrogen gas sensor is provided. The hydrogen gas sensor includes a polycarbonate substrate having hydrophobic nanostructures. The hydrogen gas sensor further includes a palladium layer in the form of nanoscale petals on the hydrophobic nanostructure. A method of making the hydrogen gas sensor is also provided. The method of making the hydrogen gas sensor includes fabricating the polycarbonate substrate. The method of making the hydrogen gas sensor further includes coating the polycarbonate substrate with the palladium layer. A method of using the hydrogen gas sensor is also provided. The method of using the hydrogen gas sensor includes contacting a palladium coated hydrophobic nanostructure of the hydrogen gas sensor with a gas sample comprising hydrogen gas.

17 Claims, 21 Drawing Sheets

(56) References Cited

OTHER PUBLICATIONS

Francisco Rumiche, et al., "Anodized aluminum oxide (AAO) nanowell sensors for hydrogen detection", Sensors and Actuators B: Chemical, vol. 134, Issue 2, Sep. 25, 2008, pp. 869-877 (Abstract only).

* cited by examiner

HYDROGEN GAS SENSOR, AND METHOD OF MAKING AND USING THEREOF

STATEMENT OF PRIOR DISCLOSURE BY THE INVENTOR

Aspects of the present disclosure are described in M. K. Hossain; "Polymer-Templated Durable and Hydrophobic Nanostructures for Hydrogen Gas Sensing Applications"; Dec. 20, 2021; Polymers, incorporated herein by reference in its entirety.

BACKGROUND

Technical Field

The present disclosure is directed to gas sensing devices; and more particularly to a hydrogen gas sensor having polymer-templated hydrophobic nanostructures, and methods of making and using such hydrogen gas sensor.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Gas sensing, particularly hydrogen gas ($H_2$) sensing has become very crucial due to its renascence as a new and alternative energy in modern life [See: Chauhan, P. S., & Bhattacharya, S. (2019). Hydrogen gas sensing methods, materials, and approach to achieve parts per billion level detection: A review. international journal of hydrogen energy, 44(47), 26076-26099; Korotcenkov, G. (2013). Handbook of gas sensor materials. Conventional approaches, 1; and Padvi, M. N., Moholkar, A. V., Prasad, S. R., & Prasad, N. R. (2021). A Critical Review on Design and Development of Gas Sensing Materials. Engineered Science, 15, 20-37]. Hydrogen is an important energy carrier that is going to be complementary to current electricity in ten next few decades [See: Kovač, A., Paranos, M., & Marciuš, D. (2021). Hydrogen in energy transition: A review. International Journal of Hydrogen Energy; and Dawood, F., Anda, M., & Shafiullah, G. M. (2020). Hydrogen production for energy: An overview. International Journal of Hydrogen Energy, 45(7), 3847-3869]. A persistence challenge is being carried out to incorporate hydrogen as fuel for "zero-emissions" vehicles, to heat accommodations and workplaces and fuel aircrafts, amongst many other applications [See: Hirscher, M., Yartys, V. A., Baricco, M., von Colbe, J. B., Blanchard, D., Bowman Jr, R. C., et al. (2020). Materials for hydrogen-based energy storage—past, recent progress and future outlook. Journal of Alloys and Compounds, 827, 153548; Sheffield, J. W., Martin, K. B., & Folkson, R. (2014). Electricity and hydrogen as energy vectors for transportation vehicles. In Alternative Fuels and Advanced Vehicle Technologies for Improved Environmental Performance (pp. 117-137). Woodhead Publishing; and Petrescu, R. V. V., Machin, A., Fontanez, K., Arango, J. C., Marquez, F. M., & Petrescu, F. I. T. (2020). Hydrogen for aircraft power and propulsion, International Journal of Hydrogen Energy].

In light of the above, not only is an efficient and sensitive sensing platform urgently needed for the safe deployment of all hydrogen-based applications, but also multifunctional capabilities are required to deal with extreme and critical environmental conditions. However, most hydrogen gas sensors, particularly used in industries and workplaces, are not suitable for advanced and sophisticated applications. The sensor needs to be smart, durable and of multitasking capacity [See: Song, Z., Ye, W., Chen, Z., Chen, Z., Li, M., Tang, W., Wang, C., Wan, Z., Poddar, S., Wen, X., Pan, X., Lin, Y., Zhou, Q. and & Fan, Z. (2021). Wireless Self-Powered High-Performance Integrated Nanostructured-Gas-Sensor Network for Future Smart Homes. ACS nano, 15(4), 7659-7667; Sazonov, E. (Ed.). (2020). Wearable Sensors: Fundamentals, implementation and applications. Academic Press; and Zhu, Z., Liu, C., Jiang, F., Liu, J., Liu, G., Ma, X., Liu, P., Huang, R., Xu, J. & Wang, L. (2021). Flexible fiber-shaped hydrogen gas sensor via coupling palladium with conductive polymer gel fiber. Journal of Hazardous Materials, 411, 125008]. The fabrication and realization of multifunctional sensing platforms have been exciting and hot areas of research in both academia and industry, including healthcare sectors and environmental protection [See: Zheng, X., & Cheng, H. (2019). Flexible and stretchable metal oxide gas sensors for healthcare. Science China Technological Sciences, 62(2), 209-223; and Soo, M. T., Cheong, K. Y., & Noor, A. F. M. (2010). Advances of SiC-based MOS capacitor hydrogen sensors for harsh environment applications. Sensors and Actuators B: Chemical, 151(1), 39-55].

In particular, there is an enticing and ever-growing interest to devise a sensing platform capable of hydrophobic and non-adhesive characteristics [See: Li, X., Gao, Z., Li, B., Zhang, X., Li, Y., & Sun, J. (2021). Self-healing superhydrophobic conductive coatings for self-cleaning and humidity-insensitive hydrogen sensors. Chemical Engineering Journal, 410, 128353; Gao, Z., Song, G., Zhang, X., Li, Q., Yang, S., Wang, T., Li, Y., Zhang, L., Guo, L. & Fu, Y. (2020). A facile PDMS coating approach to room-temperature gas sensors with high humidity resistance and long-term stability. Sensors and Actuators B: Chemical, 325, 128810; and Gao, J., Wang, L., Guo, Z., Li, B., Wang, H., Luo, J., Huang, X. & Xue, H. (2020). Flexible, superhydrophobic, and electrically conductive polymer nanofiber composite for multifunctional sensing applications. Chemical Engineering Journal, 381, 122778]. Such platforms facilitate water droplets dropped onto them rolling off automatically with a small tilt angle. In the process of rolling off, contaminants and dust are also carried away and thus the sensing surfaces become ready to detect the target gas [See: Parvate, S., Dixit, P., & Chattopadhyay, S. (2020). Superhydrophobic surfaces: insights from theory and experiment. The Journal of Physical Chemistry B, 124(8), 1323-1360; and Li, L., Bai, Y., Li, L., Wang, S., & Zhang, T. (2017). A superhydrophobic smart coating for flexible and wearable sensing electronics. Advanced Materials, 29(43), 1702517]. However, developing an artificial hydrophobic sensing surface is not that straightforward and it requires that surface becomes stable, durable, and capable to reconcile with the surrounding environment [See: Kinoshita, H., Ogasahara, A., Fukuda, Y., & Ohmae, N. (2010). Superhydrophobic/superhydrophilic micropatterning on a carbon nanotube film using a laser plasma-type hyperthermal atom beam facility. Carbon, 48(15), 4403-4408; Yilbas, B. S., Khaled, M., Abu-Dheir, N., Al-Aqeeli, N., Said, S. A. M., Ahmed, A. O. M. Ahmed, K. K. Varanasi, and Y. K. Toumi, Y. K. (2014). Wetting and other physical characteristics of polycarbonate surface textured using laser ablation. Applied surface science, 320, 21-29; Sanger, A., Kumar, A., Kumar, A., Jaiswal, J., & Chandra, R. (2016). A fast response/recovery of hydrophobic Pd/V2O5 thin films for hydrogen gas sensing. Sensors and Actuators B: Chemical, 236, 16-26; and Hassan, K., & Chung, G. S. (2017). Fast and reversible hydrogen sensing properties of Pd-capped Mg ultra-thin films modified by hydrophobic alumina substrates. Sensors and Actuators B: Chemical, 242, 450-460].

Mostly hydrophobic surface is achieved by following the improvised Cassie-Baxter model that confirms double-layer roughness wherein there should be nanoscale roughness on the top of microscale structures [See: Xie, H., & Huang, H. (2020). Gradient Wetting Transition from the Wenzel to Robust Cassie-Baxter States along Nanopillared Cicada Wing and Underlying Mechanism. Journal of Bionic Engineering, 17(5), 1009-1018; Hao, J. H., & Wang, Z. J. (2016). Modeling cassie-baxter state on superhydrophobic surfaces. Journal of Dispersion Science and Technology, 37(8), 1208-1213; and Tsougeni, K., Tserepi, A., Boulousis, G., Constantoudis, V., & Gogolides, E. (2007). Control of Nanotexture and Wetting Properties of Polydimethylsiloxane from Very Hydrophobic to Super-Hydrophobic by Plasma Processing. Plasma Processes and Polymers, 4(4), 398-405]. Although such double-layer structures have great potential in a wide range of applications including self-cleaning, anti-fouling, anti-corrosion and oil-water separation, the top nanostructures decay in time under extreme environmental conditions [See: Mortazavi, V., & Khonsari, M. M. (2017). On the degradation of superhydrophobic surfaces: A review. Wear, 372, 145-157; and Esteves, C. (2018). Self-healing functional surfaces. Advanced Materials Interfaces, 5(17), 1800293].

A wide range of organic and inorganic materials have been used as base substrates to achieve hydrophobic sensing surfaces [See: Sanjay, S. L., Annaso, B. G., Chavan, S. M., & Rajiv, S. V. (2012). Recent progress in preparation of superhydrophobic surfaces: a review. Journal of Surface Engineered Materials and Advanced Technology, 2012; Ha, C. S., & Nagappan, S. (2018). Hydrophobic and Superhydrophobic Organic-Inorganic Nano-Hybrids. CRC Press; and Quan, Y. Y., Chen, Z., Lai, Y., Huang, Z. S., & Li, H. (2021). Recent advances in fabricating durable superhydrophobic surfaces: a review in the aspects of structures and materials. Materials Chemistry Frontiers, 5(4), 1655-1682]. Polymer, particularly polycarbonate (Bisphenol A polycarbonate: 2,2-bis(p-hydroxyphenyl)-propane, PC) is one of the interesting base materials that has been studied extensively and therefore used in a wide variety of applications [See: Hoekstra, E. J., & Simoneau, C. (2013). Release of bisphenol A from polycarbonate—a review. Critical reviews in food science and nutrition, 53(4), 386-402; Shi, G. L., Li, F. S., & Tian, H. B. (2006). Advances and application of polycarbonate in automobile windows and aero glass. Mater. Rev, 404-407; Guang-hui, Z. H. A. O., Dun Jing, R. E. N., Jian-zhong, L. I., Ji-ming, S. U. N., Xin, L. I. U., & Yong, C. H. E. N. (2005). Production, Application and Market Prospect of Polycarbonate [J]. Chemical Technology Market, 5; and ZHANG, Y., ZHU, S. F., XIA, X. L., & WANG, H. X. (2010). Synthesis Technologies and Application Progress of Polycarbonate [J]. Liaoning Chemical Industry, 6]. Due to low-cost, high durability, low modulus of elasticity, and high transparency, polycarbonate (PC) has been useful in optoelectronic and microelectronic applications [See: Subramani, N. K., Shivanna, S., Nagaraj, S. K., Suresha, B., Raj, B. J., & Siddaramaiah, H. (2018). Optoelectronic Behaviours of UV shielding Calcium Zirconate Reinforced Polycarbonate Nanocomposite Films: An Optical View. Materials Today: Proceedings, 5(8), 16626-16632; Bormashenko, E., Pogreb, R., Stanevsky, O., Biton, Y., & Bormashenko, Y. (2004). Self-organization in thin polycarbonate films and its optical and electro-optical applications. Journal of materials science, 39(21), 6639-6641; and Goyal, P. K., Kumar, V., Gupta, R., Mahendia, S., & Kumar, S. (2012). Modification of polycarbonate surface by Ar+ ion implantation for various opto-electronic applications. Vacuum, 86(8), 1087-1091].

Polycarbonate (PC) is an industrially-attractive polymer material that is being extracted as a by-product from oil and gas refineries through industrial scale and low-cost processes [See: Fukuoka, S., Fukawa, I., Adachi, T., Fujita, H., Sugiyama, N., & Sawa, T. (2019). Industrialization and Expansion of Green Sustainable Chemical Process: A Review of Non-phosgene Polycarbonate from CO2. Organic Process Research & Development, 23(2), 145-169; and Kamps, J. H., Scheffler, C., Simon, F., van der Heijden, R., & Verghese, N. (2018). Functional polycarbonates for improved adhesion to carbon fibre. Composites Science and Technology, 167, 448-455]. However, it has been found that such PC may be further reinforced by including hydrophobic characteristics that is a key element in many applications that requires self-cleaning property. It is well-acknowledged that the effectiveness of hydrophobicity is demonstrated by the Cassie-Baxter model, and the same model indicates a higher surface area that is required for many surface-enhanced applications, such as molecule detection and sensing [See: Li, G. J., & Kawi, S. (1998). High-surface-area $SnO_2$: a novel semiconductor-oxide gas sensor. Materials Letters, 34(1-2), 99-102; Ikram, M., Liu, L., Liu, Y., Ma, L., Lv, H., Ullah, M., . . . & Shi, K. (2019). Fabrication and characterization of a high-surface area MoS 2@ WS 2 heterojunction for the ultra-sensitive $NO_2$ detection at room temperature. Journal of Materials Chemistry A, 7(24), 14602-14612; and Shen, Y., Yamazaki, T., Liu, Z., Meng, D., Kikuta, T., & Nakatani, N. (2009). Influence of effective surface area on gas sensing properties of WO3 sputtered thin films. Thin Solid Films, 517(6), 2069-2072]. For multifunctional devices, particularly hydrophobic gas sensing platforms using PC as base materials is industrially viable and one of the promising candidates.

However, PC-templated hydrophobic gas sensing platform has not been reported in the art. Mazen et al. [See: Khaled, M. (2015). Directed hierarchical patterning of polycarbonate bisphenol a glass surface along predictable sites. Journal of Nanomaterials, 2015] demonstrated and devised a transparent hydrophobic PC as a self-cleaning surface for PV panels installed in a dusty environment. Yilbas et al. [See: Yilbas, B. S., Ali, H., Al-Aqeeli, N., Khaled, M., Abu-Dheir, N., & Varanasi, K. K. (2016). Solvent-induced crystallization of a polycarbonate surface and texture copying by polydimethylsiloxane for improved surface hydrophobicity. Journal of Applied Polymer Science, 133(22)] developed a generic process to copy the micro/nanoscale structure of hydrophobic PC by PDMS that showed higher WCA and transparency. Jhang et al. [See: Jang, M., Park, C. K., & Lee, N. Y. (2014). Modification of polycarbonate with hydrophilic/hydrophobic coatings for the fabrication of microdevices. Sensors and Actuators B: Chemical, 193, 599-607] developed hydrophobic microchannels in PC that enabled valve-free sequential injection of multiple liquids. Most of the methods used in achieving such hydrophobic PC were associated with multiple treatments apart from the requirement of skilled hands and the usage of specialized reagents.

Further, US Patent Document No. 8052898B2 discloses a hydrogen gas detecting material, which changes in light absorption characteristics when exposed to an atmosphere containing hydrogen, and a coating method in which the principal component of the hydrogen gas detecting material is tungsten oxide, palladium is deposited on the surface of the tungsten oxide, the tungsten oxide is coated on a substrate by a sputtering method involving a controlled oxygen pressure, and the temperature of the substrate during coating with the tungsten oxide is room temperature (20° C.).

EP Patent Document No. 2010894B1 relates to a hydrogen sensor with a radiation source, by means of which electromagnetic radiation is radiated onto a sensor medium, wherein the sensor medium has a transmission coefficient that varies as a function of the concentration of hydrogen in the environment of the sensor medium, and with a detector that detects at least a portion of the radiation transported through the sensor medium. The hydrogen sensor according to this reference is characterized by the fact that the sensor medium incorporates clusters containing or consisting of a palladium alloy, yttrium, scandium, at least one lanthanide, at least one actinide, tungsten oxide and/or vanadium oxide, and/or a mixture or compound of these materials.

KR Patent Publication No. 20170086786A relates to a hydrogen gas sensor after manufacturing graphene with floral palladium introduced by using surface modification and electrolytic plating, and introducing a functional group to the graphene surface using a reforming solution. This reference also provides a method for producing graphene in which flower-shaped palladium is finally introduced by introducing flower-shaped palladium on the surface of graphene by electrolytic plating using the prepared reformed graphene as a working electrode.

Non-Patent Literature Document titled "Palladium on Plastic Substrates for Plasmonic Devices" relates to innovative chips based on palladium thin films deposited on plastic substrates, which have been tested in the Kretschmann surface plasmon resonance (SPR) configuration. This document describes that said chips combine the advantages of a plastic support that is interesting and commercially appealing and the physical properties of palladium, showing inverted surface plasmon resonance (ISPR).

Non-Patent Literature Document titled "Flexible Palladium-Based $H_2$ Sensor with Fast Response and Low Leakage Detection by Nanoimprint Lithography" relates to flexible palladium-based $H_2$ sensors. This document demonstrates, using direct nanoimprint lithography of palladium, the fabrication of a $H_2$ sensor that is capable of detecting $H_2$ gas concentration as low as 50 ppm. The document describes that high resolution and high throughput patterning of palladium gratings over a 2 cm×1 cm area on a rigid substrate was achieved by heat-treating nanoimprinted palladium benzyl mercaptide at 250° C. for 1 h, and the $H_2$ sensing device was fabricated by subsequent transfer nanoimprinting of these gratings into a polycarbonate film at its glass transition temperature.

Non-Patent Literature Document titled "Anodized aluminum oxide (AAO) nanowell sensors for hydrogen detection" relates to fabrication of a nanostructured sensing device based on anodic aluminum oxide (AAO) nanowells and investigated for hydrogen gas sensing. The document describes that AAO nanowells with an average pore diameter of 73 nm and with 2, 6, and 12 min anodization time which were immersed in a surfactant solution and coated with an 8 nm film of palladium nanoparticles. This document utilizes the electrical resistance change of the nanostructured sensor with hydrogen gas exposure as the sensing parameter.

Each of the aforementioned references suffers from one or more drawbacks hindering their adoption. None of the references provides a hydrogen gas sensing platform which has high hydrophobicity and good gas sensing characteristics, while allowing for a simple and a low-cost manufacturing process. It is an object of the present disclosure to provide a hydrogen gas sensor having polymer-templated hydrophobic nanostructures providing excellent hydrophobicity as well as superior gas sensing characteristics, and which can be manufactured by a simple and hands-on industrial scale process.

SUMMARY

In an exemplary embodiment, a hydrogen gas sensor is provided. The hydrogen gas sensor comprises a polycarbonate substrate having hydrophobic nanostructures. The hydrogen gas sensor further comprises a palladium layer in the form of nanoscale petals on the hydrophobic nanostructure.

In one or more exemplary embodiments, the nanostructure determined by 2D topographic mapping has a maximum step height along a horizontal line scan in a range of 3 to 17 µm. Also, the nanostructure determined by 2D topographic mapping has a minimum step height along a horizontal line scan in a range of −28 to −14 µm. Further, the nanostructure determined by 2D topographic mapping has hills in a line scan along a vertical axis in a range of 6 to 20 µm. Furthermore, the nanostructure determined by 2D topographic mapping has dips in a line scan along a vertical axis in a range of −30 to −13 µm.

In one or more exemplary embodiments, the polycarbonate substrate has a wetting contact angle in a range of 112.0° to 162.0°.

In one or more exemplary embodiments, the hydrophobic nanostructures and the palladium layer form a double-layer structure.

In one or more exemplary embodiments, the nanoscale petals are arranged in the form of microscopic flowers. In one or more exemplary embodiments, the microscopic flowers are on a surface. In one or more exemplary embodiments, the nanoscale petals have an average length in a range of 1 to 10 µm with an average width in a range of 100 to 800 nm. In one or more exemplary embodiments, the nanoscale petals have an average length in a range of 1 to 2.5 µm with an average width in a range of 150 to 450 nm.

In another exemplary embodiment, a method of making the hydrogen gas sensor is provided. The method of making the hydrogen gas sensor comprises fabricating the polycarbonate substrate. The method of making the hydrogen gas sensor further comprises coating the polycarbonate substrate with the palladium layer.

In one or more exemplary embodiments, the polycarbonate substrate is fabricated with a wet chemical treatment, for making the hydrogen gas sensor.

In one or more exemplary embodiments, the palladium layer is coated with a sputtering technique, for making the hydrogen gas sensor.

In another exemplary embodiment, a method of using the hydrogen gas sensor is provided. The method of using the hydrogen gas sensor comprises contacting a palladium coated hydrophobic nanostructure of the hydrogen gas sensor with a gas sample comprising hydrogen gas.

In one or more exemplary embodiments, the gas sample has a temperature of 0 to 50° C., for using the hydrogen gas sensor.

In one or more exemplary embodiments, the hydrogen gas sensor has a repeatability of at least 99%.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
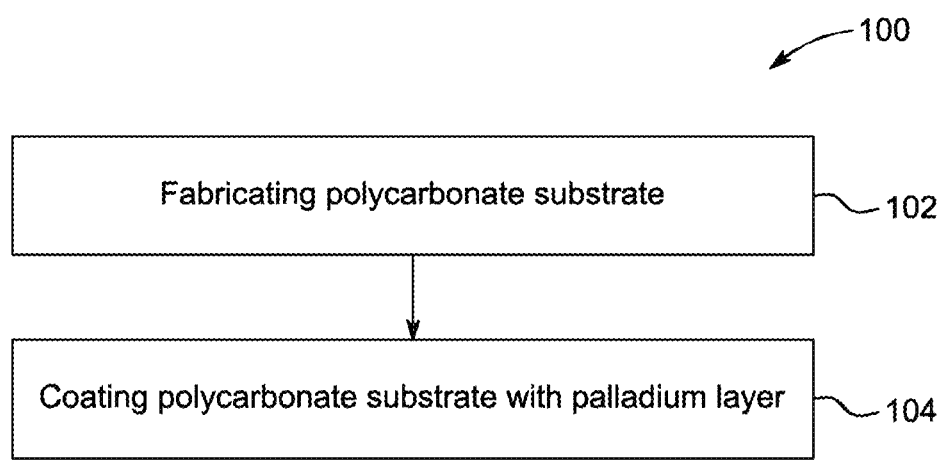
FIG. 1 is a flowchart of a method of making a hydrogen gas sensor, according to certain embodiments.

The present disclosure will be better understood with reference to the following definitions.

It will be understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

In the drawings, like reference numerals designate identical or corresponding parts throughout the several views. Further, as used herein, the words "a," "an" and the like generally carry a meaning of "one or more," unless stated otherwise. Also, the use of "or" means "and/or" unless stated otherwise. Similarly, "comprise," "comprises," "comprising" "include," "includes," and "including" are interchangeable and not intended to be limiting.

Furthermore, the terms "approximately," "approximate," "about," and similar terms generally refer to ranges that include the identified value within a margin of 20%, 10%, or preferably 5%, and any values there between. For example, if a stated value is about 8.0, the value may vary in the range of 8±1.6, ±1.0, ±0.8, ±0.5, ±0.4, ±0.3, ±0.2, or ±0.1.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

According to a first aspect, the present disclosure relates to a hydrogen gas sensor comprising polymer-templated hydrophobic nanostructures. The hydrogen gas sensor comprises a polycarbonate substrate having hydrophobic nanostructures and a palladium layer in the form of nanoscale petals on the hydrophobic nanostructures. In one embodiment, the polycarbonate substrate has a wetting contact angle in a range of 80° to 200°, preferably 90° to 180°, preferably 100° to 170°, preferably 112.0° to 162.0°.

In one embodiment, the substrate may be planar, and may have a rectangular shape, a circular shape, or some other shape. In one embodiment, the substrate may have a planar side with a surface area of 0.1-100 cm², preferably 0.25-50 cm², more preferably 0.5-10 cm², even more preferably 0.7-8 cm². However, in some embodiments, the substrate may have a planar side with a surface area smaller than 0.1 cm² or larger than 100 cm². The substrate may have a thickness of 0.10-20 mm, preferably 0.15-15 mm, more preferably 0.17-10 mm, however, in some embodiments, the substrate may have a thickness of less than 0.10 mm, or greater than 20 mm. In an alternative embodiment, the substrate may be curved, grooved, knurled, or shaped into some other non-planar arrangement.

In some embodiments, microscopic flowers described herein may be called "nanoflowers". As used herein, microscopic flowers are particles exhibiting a characteristic three-dimensional flower-like morphology. In one embodiment, microscopic flowers comprise 1 to 100 overlapping nano petals. In one embodiment, microscopic flowers comprise 1 to 100 nano petals without overlapping.

In one embodiment, the hydrophobic nanostructures and the palladium layer form a double-layer structure. In one embodiment, the nanoscale petals are arranged in the form of microscopic flowers. In one embodiment, the microscopic flowers are on a surface of the hydrophobic nanostructures. In one embodiment, the nanoscale petals have an average length in a range of 0.1 to 50 µm, preferably 0.5 to 40 µm, preferably 0.5 to 30 µm, preferably 0.8 to 20 µm, preferably 1 to 15 µm, preferably 1 to 10 µm, preferably 1 to 2.5 µm with an average width in a range of 50 to 1200 nm, preferably 70 to 1000 nm, preferably 80 to 900 nm, preferably 100 to 800 nm, preferably 150 to 450 nm.

The cross-section of the nanopetals present in the nanoflowers may be of any desired shape, such as a circle, an oval, an ellipse, a multilobe, and a polygon. In a preferred embodiment, the cross-section of the nanopetals is oval shaped, preferably a twisted oval shape with pairs of opposing ends out of plane. The oval may optionally have one or more axes of symmetry.

In an alternative embodiment, the nanopetals may be rod-shaped. In a related embodiment, the nanopetals are uniform throughout the entire length of the nanopetals and are of a cylindrical shape. In another embodiment, the nanopetals are conical-shaped or elongated oval-shaped (cigar-shaped). Alternatively, the nanopetals have oval or polygonal shaped cross-sections with diameters that taper along the length of the nanopetals to a rounded tip.

In one embodiment, the hydrophobic nanostructures have a maximum step height along a horizontal line scan in a range of 1 to 30 µm, preferably 2 to 20 µm, preferably 3 to 17 µm determined by 2D topographic mapping.

In one embodiment, the hydrophobic nanostructures have a minimum step height along a horizontal line scan in a range of −35 to −10 µm, preferably −30 to −12 µm, preferably −28 to −14 µm determined by 2D topographic mapping.

In one embodiment, the hydrophobic nanostructures have hills in a line scan along a vertical axis in a range of 1 to 40 µm, preferably 3 to 30 µm, preferably 6 to 20 µm determined by 2D topographic mapping.

In one embodiment, the hydrophobic nanostructures have dips in a line scan along a vertical axis in a range of −40 to −8 µm, preferably −35 to −10 µm, preferably −30 to −13 µm determined by 2D topographic mapping.

According to a second aspect, the present disclosure relates to a method of making the hydrogen gas sensor of the first aspect. The hydrogen gas sensor of the present disclosure is preferably made by a simple and an inexpensive process involving hydrophobic polycarbonate (PC) substrate fabricated by a wet chemical treatment being coated with palladium (Pd), preferably by high vacuum sputtering technique.

According to a third aspect, the present disclosure relates to a method of using the hydrogen gas sensor of the first aspect. This method involves contacting the hydrogen gas sensor with a gas sample comprising hydrogen gas.

In one embodiment, the gas sample has a temperature of 0-80° C., preferably 0-70° C., preferably 0-50° C. However, in some embodiments, the gas sample may have a temperature of less than 0° C. or greater than 50° C.

In one embodiment, the hydrogen gas sensor has a repeatability of at least 99%.

The present disclosure further provides an apparatus for a sensing arrangement to carry out tests for determining sensing performance of the fabricated hydrogen gas sensor, which reveals a dual role in hydrophobicity as well as superior gas sensing characteristics.

Referring to FIG. 1, illustrated is a flowchart of a method (represented by reference numeral 100) of making a hydrogen gas sensor, according to certain embodiments. The hydrogen gas sensor of the present disclosure provides a multifunctional sensing platform for extreme environmental conditions.

Although the present disclosure has been described in terms of a hydrogen gas sensor for hydrogen gas ($H_2$) sensing applications, it will be appreciated by a person skilled in the art that teachings of the present disclosure may generally be applied for other types of gas (or fluid) sensors with some or without any modifications (as may be contemplated), including that of the method 100 for making (fabrication) of the said other types of sensors, without departing from the spirit and the scope of the present disclosure. Thereby, the term "hydrogen gas sensor" as used in the context of the present disclosure has sometimes been broadly referred using the term "sensor" without any limitations.

The method 100 provides a simple and a low-cost process to fabricate the present hydrogen gas sensor. The method 100 may allow for industrial-scale production of the hydrogen gas sensor as would be needed for the safe deployment of all hydrogen-based applications, with the fabricated hydrogen gas sensor providing multifunctional capabilities as required to deal with extreme and critical environmental conditions. It will be appreciated that steps described hereinafter in reference to the method 100 are only illustrative, and other alternatives may also be provided where one or more steps are re-ordered, one or more steps are added/removed without departing from the spirit and the scope of the present disclosure.

EXAMPLES

High-resolution field-emission scanning electron microscopy (FE SEM) of the fabricated hydrogen gas sensor revealed double-layer structures consisting of fine microscopic flower-like structures of nanoscale petals on the top of base nanostructures.

Sessile drop tests of the fabricated hydrogen gas sensor confirmed wetting contact angle (WCA) of the implemented Pd-decorated PC to be ~110°±50.0°, preferably ~110°±40.0°, preferably ~110°±30.0°, preferably ~120°±20.0°, preferably ~130°±10.0°, which is found to be suitable for hydrogen sensing applications.

Figure 2A:
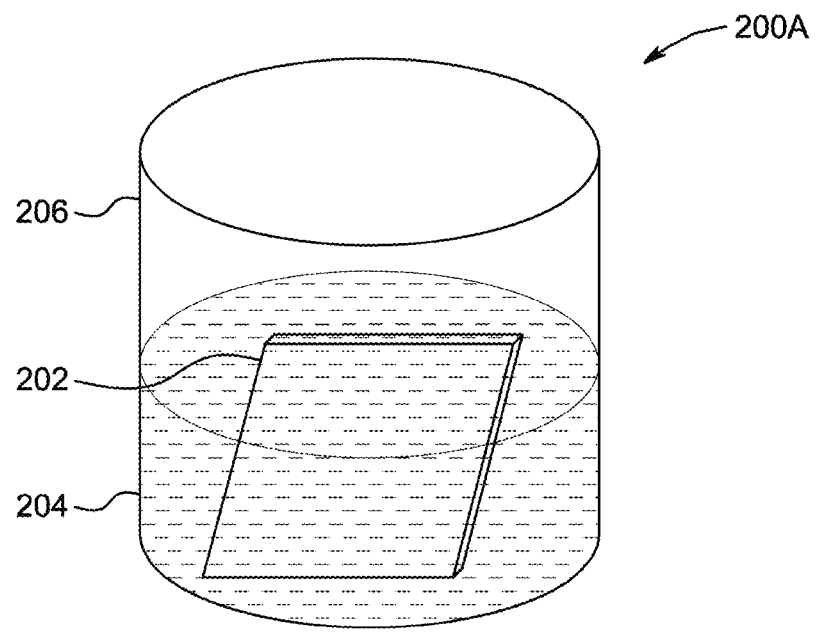
FIG. 2A is an illustration of a first processing stage in fabrication of the hydrogen gas sensor, to process a polycarbonate sample to form a pristine polycarbonate sample, according to certain embodiments.

At step 102, the method 100 includes fabricating a polycarbonate substrate. Referring to FIGS. 2A, 2C and 2E in combination, illustrated are different processing stages in fabrication of the hydrogen gas sensor.

FIG. 2A illustrates a first processing stage (represented by reference numeral 200A) in fabrication of the hydrogen gas sensor. In the first processing stage 200A, as shown in FIG. 2A, a PC sample (represented by reference numeral 202) is first treated with a chemical solution (represented by reference numeral 204) under controlled lab conditions. Herein, the PC sample 202 may be immersed in a container 206 filled with the chemical solution 204 for such treatment. In an example, the chemical solution 204 is polar aprotic solvent such as acetone, acetonitrile, dichloromethane, dimethylformamide, ethyl acetate, and tetrahydrofuran, preferably dichloromethane and exposed to a vapor phase polar aprotic solvent, such as acetone thus obtaining a textured surface with a hierarchical patterned nanoporous structure wherein the textured surface has a higher surface hydrophobicity and a marginally reduced optical light transmittance relative to the polycarbonate surface prior to the immersion, the exposure, or both. Thereafter, the PC sample 202 may be washed to remove the excess chemical solution 204. Herein, the PC sample 202 may be washed copiously with deionized (DI) water.

Figure 2B:
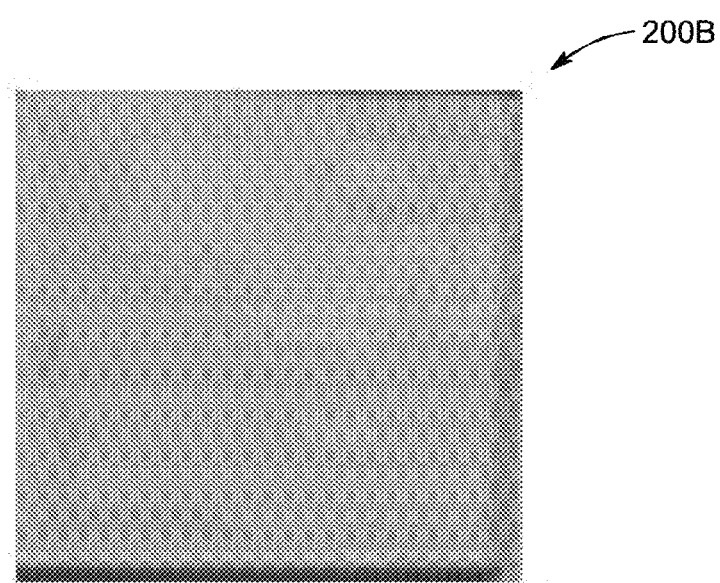
FIG. 2B is a Charge Coupled Device (CCD) image of the formed pristine polycarbonate sample, according to certain embodiments.
Figure 2C:
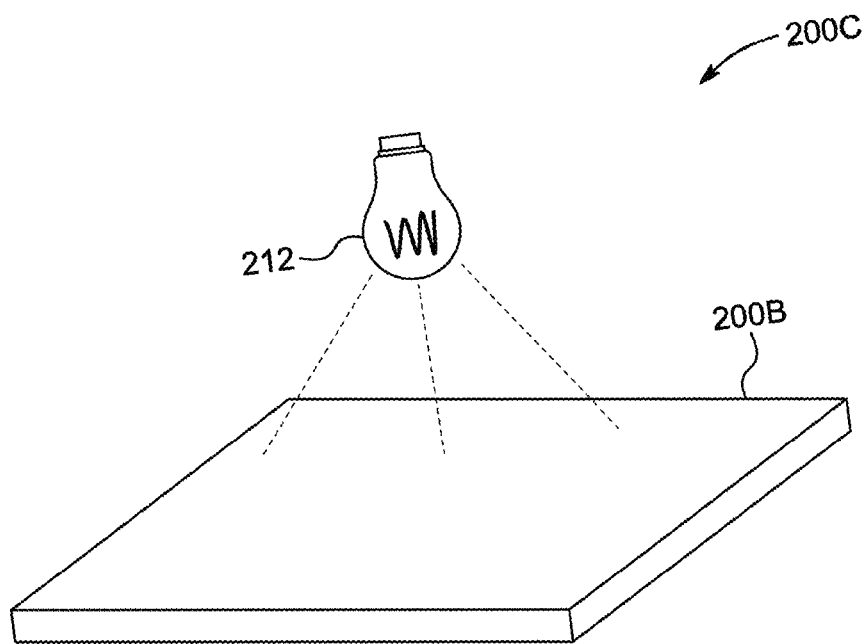
FIG. 2C is an illustration of a second processing stage in fabrication of the hydrogen gas sensor, to process the formed pristine polycarbonate sample to a treated polycarbonate sample, according to certain embodiments.

FIG. 2B is a Charge Coupled Device (CCD) image of the formed pristine PC sample (represented by reference numeral 200B).

Figure 2D:
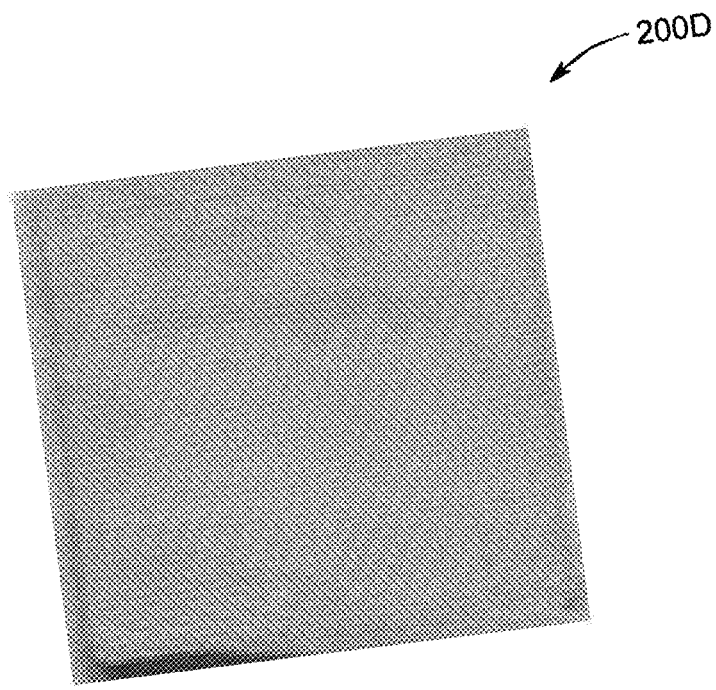
FIG. 2D is a CCD image of the treated polycarbonate sample, according to certain embodiments.
Figure 2E:
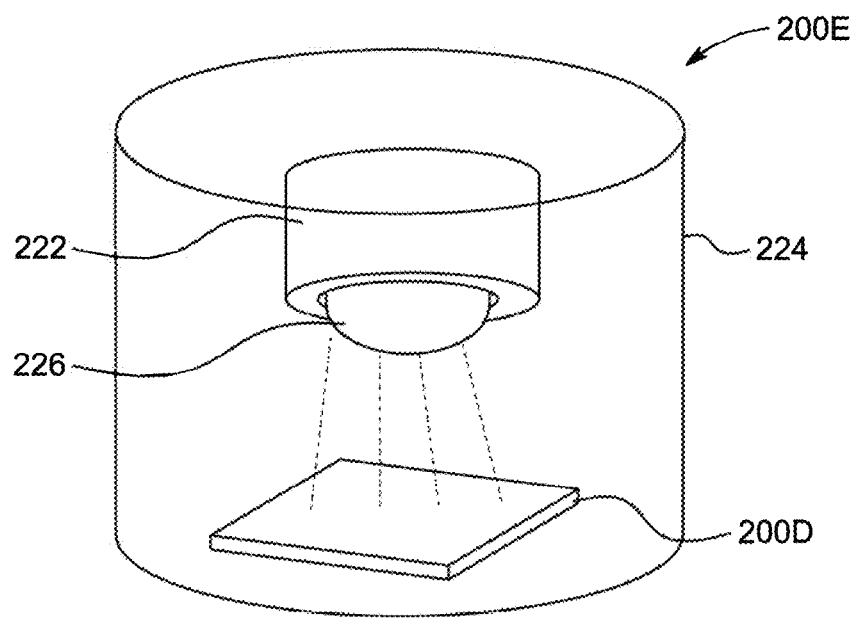
FIG. 2E is an illustration of a third processing stage in fabrication of the hydrogen gas sensor, to process the treated polycarbonate sample to a Palladium-decorated polycarbonate substrate, according to certain embodiments.

FIG. 2C illustrates a second processing stage (represented by reference numeral 200C) in fabrication of the hydrogen gas sensor. In the second processing stage 200C, as shown in FIG. 2C, the pristine PC sample 200B (as obtained after completion of the first processing stage 200A) is exposed to a light source 212 to dry before transferring to an automatic sputtering coater. In an example, the implemented light source 212 may be a fluorescent light of about 20 to 40 watts, preferably 25 to 35 watts, preferably 30 watts (W). Herein, the pristine PC sample 200B may be left under the light source 212 for about 5 to 40 minutes, preferably 5 to 30 minutes, preferably 5 to 20 minutes, preferably 10 minutes. The second processing stage 200C leads to completion of the treatment process and results in a treated PC sample. FIG. 2D is a CCD image of the formed treated PC sample (represented by reference numeral 200D).

Figure 2F:
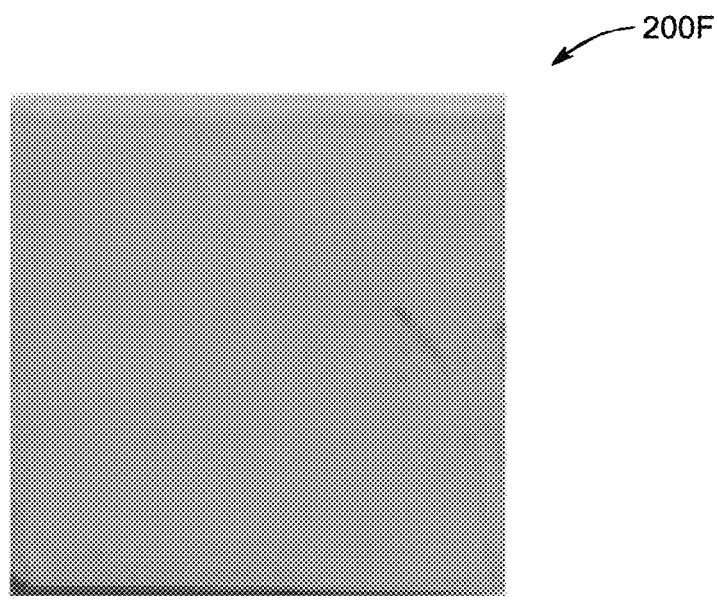
FIG. 2F is a CCD image of the Palladium-decorated polycarbonate substrate, according to certain embodiments.

Referring back to FIG. 1, at step 104, the method 100 includes coating the polycarbonate substrate (i.e., the treated PC sample 200D) with a palladium layer. In an embodiment, the palladium layer is coated with a sputtering technique. FIG. 2E illustrates a third processing stage (represented by reference numeral 200E) in fabrication of the hydrogen gas sensor. In the third processing stage 200E, as shown in FIG. 2E, the treated PC sample 200D (as obtained after completion of the second processing stage 200C) is transferred to an automatic sputtering coater 222 (such as Thomasnet model #NSC 4000). As shown, the automatic sputtering coater 222 is disposed in a chamber 224. Herein, the automatic sputtering coater 222 is implemented for palladium (Pd) decoration of the treated PC sample 200D. For this purpose, a Pd target 226 of high purity (99.999%) may be utilized, as available from Semiconductor Wafer Inc. and used as received without any modification. In an example, a distance between the Pd target 226 and the treated PC sample 200D is fixed at about 5 to 20 cm, preferably 5 to 15 cm, preferably 10 cm. In the third processing stage 200E, the automatic sputtering coater 222 is used to generate plasma by direct current (DC) magnetron power of about 20 to 40 W, preferably 25 to 35 W, preferably 30 W for about 5 to 40 seconds, preferably 10 to 30 seconds, preferably 20 seconds keeping a background pressure in the chamber 224 as low as 1.5 to $5 \times 10^{-6}$ Torr, preferably 2 to $4 \times 10^{-6}$ Torr, preferably $3.5 \times 10^{-6}$ Torr in Argon gas flow of 50 to 100 SCCM, preferably 60 to 90 SCCM, preferably 80 SCCM (standard cubic centimeters per minute). In some examples, the third processing stage 200E may also involve pre-sputtering for cleaning the Pd target 226, which may be carried out for about 30 seconds to 5 minutes, preferably 1 to 4 minutes, preferably 1 to 3 minutes, preferably 1 minute. The third processing stage 200E results in a Pd-decorated PC substrate. FIG. 2F is a CCD image of the formed Pd-decorated PC substrate (represented by reference numeral 200F).

In the present embodiments, the Pd-decorated PC substrate 200F acts as the hydrogen gas sensor, and as such, hereinafter, the hydrogen gas sensor has been referred by the same reference numeral (i.e., as hydrogen gas sensor 200F). The hydrogen gas sensor 200F of the present disclosure includes the palladium coated polycarbonate substrate having hydrophobic nanostructures. Further, in the present embodiments, the hydrogen gas sensor 200F includes the palladium layer in the form of nanoscale petals on a hydrophobic base nanostructure. Such structural details for the hydrogen gas sensor 200F have been explained in detail in the proceeding paragraphs.

Figure 3A:
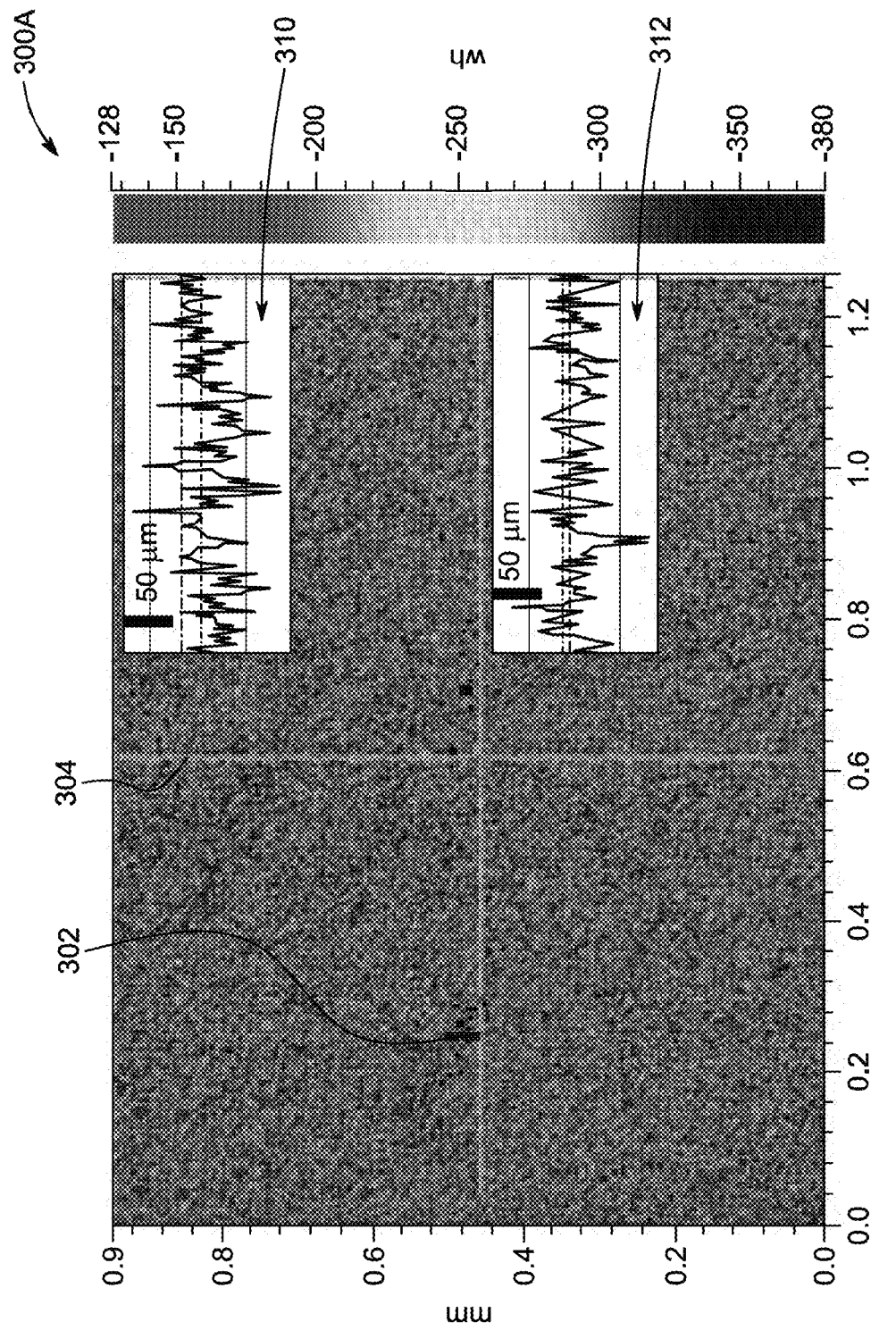
FIG. 3A is a 3D optical microscope image of the hydrogen gas sensor, according to certain embodiments.

Referring now to FIG. 3A, illustrated is a 3D optical microscope image (as represented by reference numeral 300A) of the hydrogen gas sensor (such as, the hydrogen gas sensor 200F). Herein, the 3D optical microscope image 300A may allow to perform a quick screening and an initial assessment of surface of the hydrogen gas sensor 200F. In the present examples, the 3D optical microscope image 300A may be captured by using a 3D optical microscope (such as Meiji Techno model #MX7100). In the present examples, the said 3D optical microscope may implement infinity-corrected optics for reflected light observation, and thus facilitate acquisition of long-range line scans from the 3D optical microscope image 300A of the hydrogen gas sensor 200F.

Figure 3B:
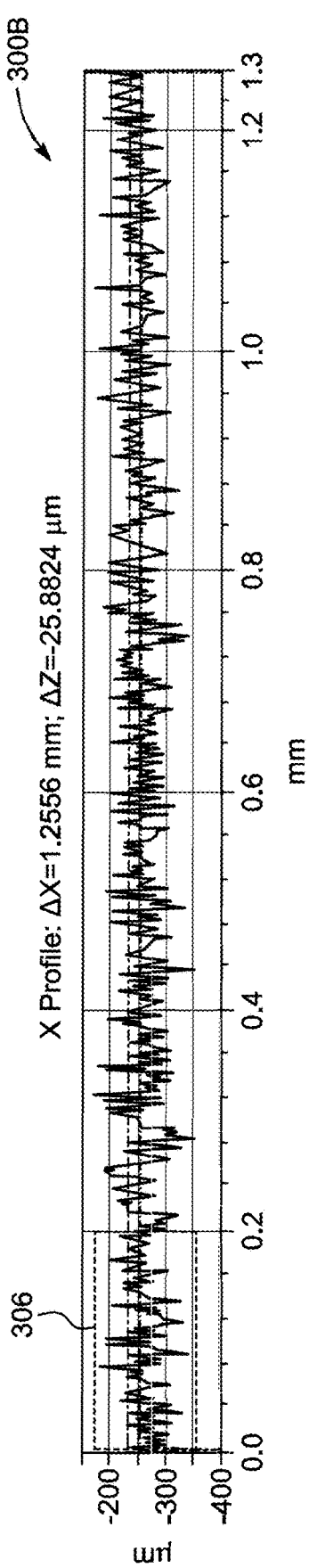
FIG. 3B is a graph representing long-range line scans of the 3D optical microscope image of FIG. 3A along a horizontal axis thereof, according to certain embodiments.
Figure 3C:
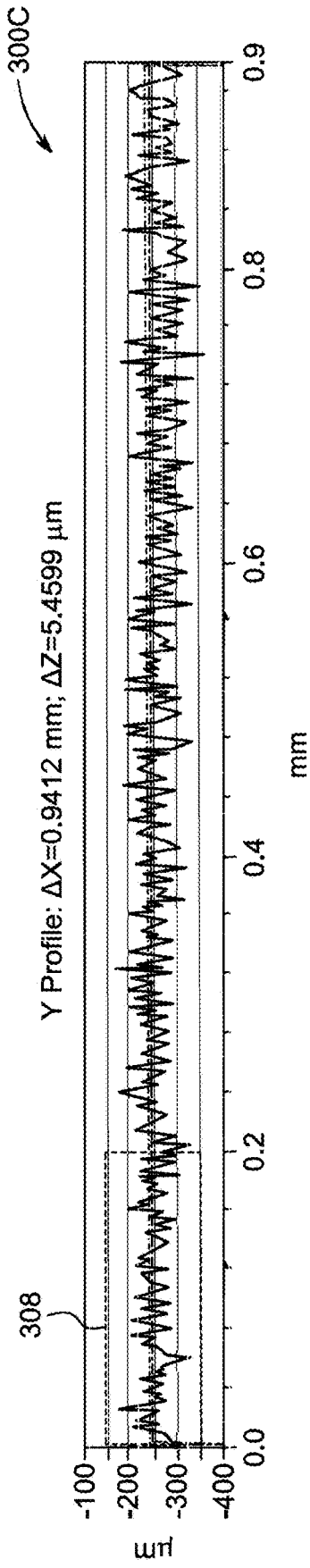
FIG. 3C is a graph representing long-range line scans of the 3D optical microscope image of FIG. 3A along a vertical axis thereof, according to certain embodiments.

FIG. 3B and FIG. 3C illustrate graphs representing detailed long-range line scans 300B and 300C along a horizontal axis 302 (as shown in FIG. 3A) and a vertical axis 304 (as shown in FIG. 3A), respectively, of the 3D optical microscope image 300A of FIG. 3A. Further, a zoomed-in view of a portion 306 (as represented by dashed rectangle) in the long-range line scan 300B is shown as an inset 308 in FIG. 3A. Similarly, a zoomed-in view of a portion 310 (as represented by dashed rectangle) in the long-range line scan 300C is shown as an inset 312 in FIG. 3A. As may be noted by a person skilled in the art, the long-range line scans 300B, 300C, and in particular the corresponding zoomed-in views as shown in the insets 308, 312, provide an impression that the hydrogen gas sensor 200F may have microscale roughness.

Figure 3D:
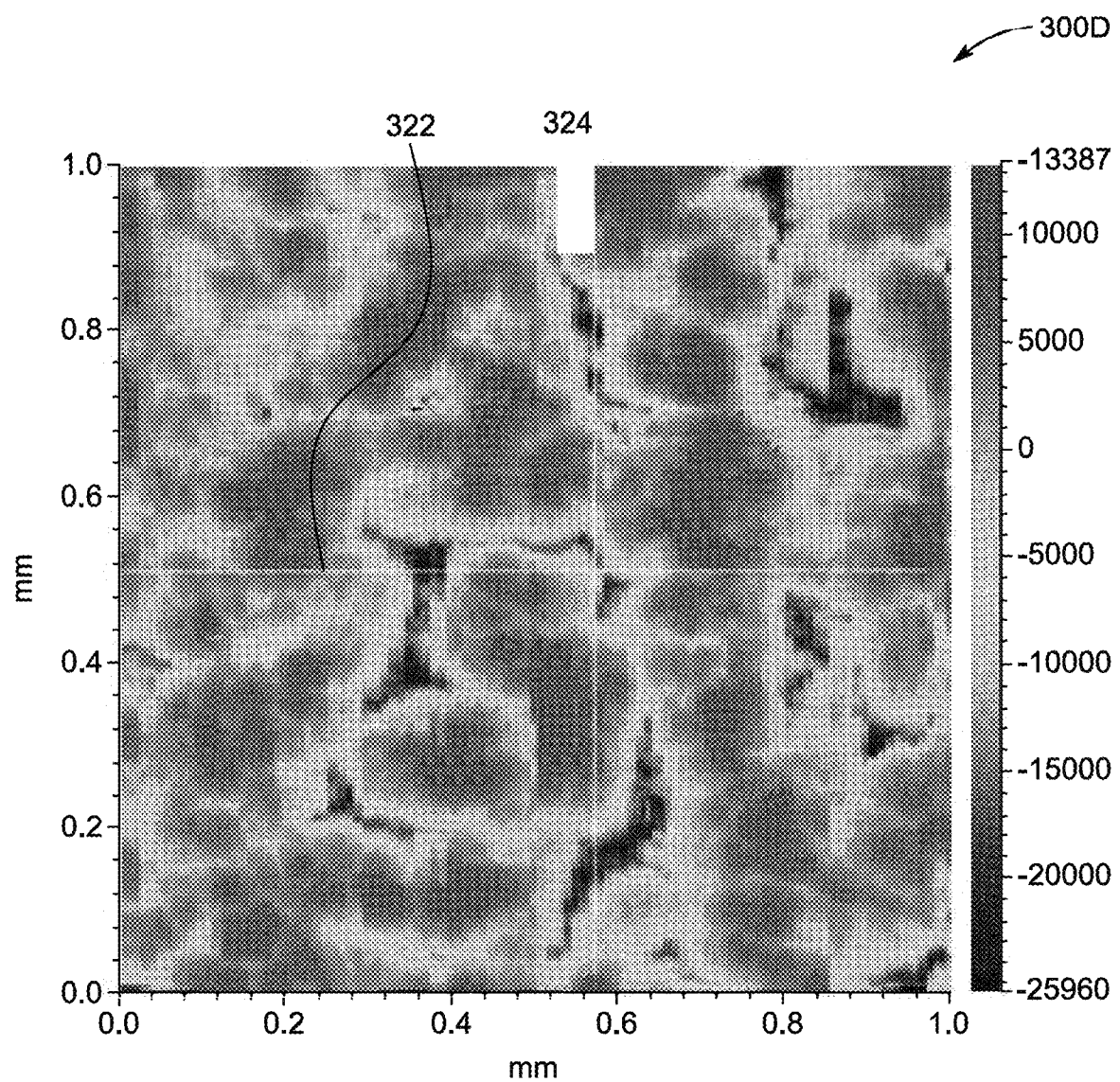
FIG. 3D is a 2D topographic mapping image of the hydrogen gas sensor, according to certain embodiments.

Referring to FIG. 3D, illustrated is a 2D topographic mapping image (as represented by reference numeral 300D) of the hydrogen gas sensor (such as, the hydrogen gas sensor 200F).

Herein, the 2D topographic mapping image 300D may allow to study details of the surface topography of the hydrogen gas sensor 200F. In the present examples, the 2D topographic mapping image 300D may be captured by using a surface profilometer (such as Dektak profilometer). The Dektak profilometer is used to explore microscopic surface structure of the hydrogen gas sensor 200F to obtain the 2D topographic mapping image 300D. In particular, as may be understood, the Dektak profilometer employs a surface contact measurement technique, where a very low force stylus is dragged across a surface to measure step heights or trench depths on a surface. As may be observed by a person skilled in the art, the 2D topographic mapping image 300D indicates step height in nanostructure of the hydrogen gas sensor 200F (as may be traced by the stylus).

Figure 3E:
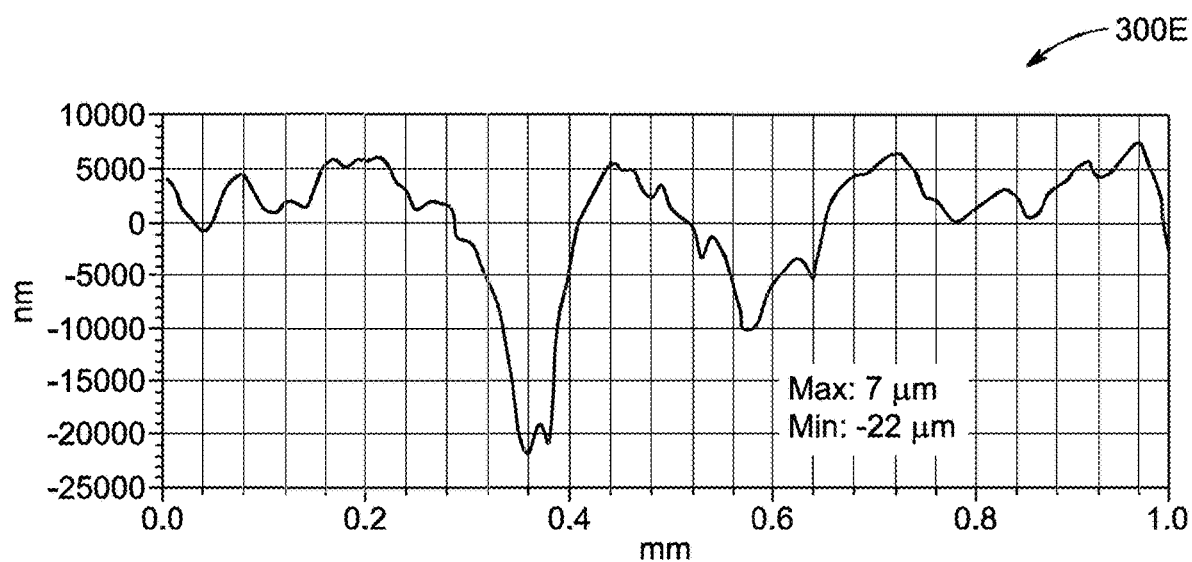
FIG. 3E is a graph representing long-range line scans of the 2D topographic mapping image of FIG. 3D along a horizontal axis thereof, according to certain embodiments.
Figure 3F:
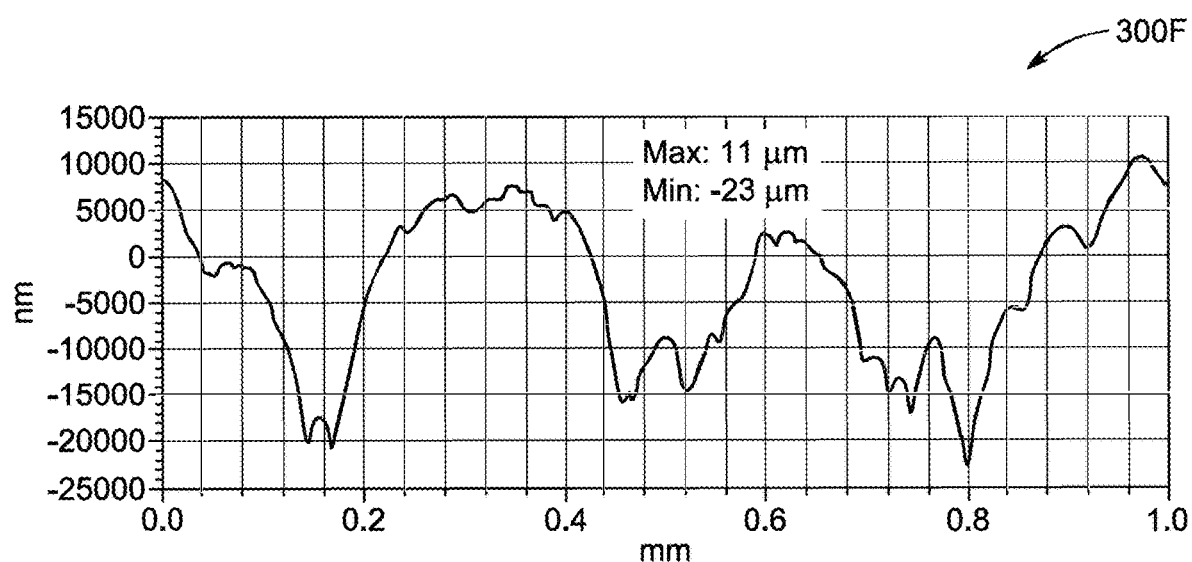
FIG. 3F is a graph representing long-range line scans of the 2D topographic mapping image of FIG. 3D along a vertical axis thereof, according to certain embodiments.

FIG. 3E and FIG. 3F illustrate graphs representing long-range line scans 300E and 300F along a horizontal axis 322 (as shown in FIG. 3D) and a vertical axis 324 (as shown in FIG. 3D), respectively, of the 2D topographic mapping image 300D of FIG. 3D. As may be observed, hills and dips are visible in both of the long-range line scans 300E and 300F. In the present embodiments, the nanostructure determined by the 2D topographic mapping (i.e., the 2D topographic mapping image 300D) has a maximum step height along a horizontal line scan (i.e., the long-range line scan 300E along the horizontal axis 322) in a range of 1 to 20 µm, preferably 2 to 19 µm, preferably 3 to 18 µm, preferably 3 to 17 µm. Further, the nanostructure determined by the 2D topographic mapping (i.e., the 2D topographic mapping image 300D) has a minimum step height along the horizontal line scan in a range of −30 to −20 µm, preferably −29 to −18 µm, preferably −28 to −14 µm. In particular, the maximum step height and the minimum step height along the horizontal line scan are determined to be about 3 to 15 µm, preferably 4 to 13 µm, preferably 5 to 10 µm, preferably 7 µm and −30 to −20 µm, preferably −25 to −21 µm, preferably −22 µm, respectively. Also, in the present embodiments, the nanostructure determined by the 2D topographic mapping (i.e., the 2D topographic mapping image 300D) has hills in the line scan 300F along the vertical axis 234 in a range of 3 to 35 µm, preferably 4 to 30 µm, preferably 5 to µm, preferably 6 to 20 µm. Further, the nanostructure determined by the 2D topographic mapping (i.e., the 2D topographic mapping image 300D) has dips in the line scan 300F along the vertical axis 234 in a range of −40 to −10 µm, preferably −35 to −11 µm, preferably −30 to −13 µm. In particular, in the case of the line scan 300F along the vertical axis 234 of the 2D topographic mapping image 300D, such hills and dips are determined to be about 8 to 15 µm, preferably 9 to 13 µm, preferably 11 µm and −30 to −20 µm, preferably −28 to −20 µm, preferably −25 to −20 µm, preferably −23 µm, respectively.

Figure 3G:
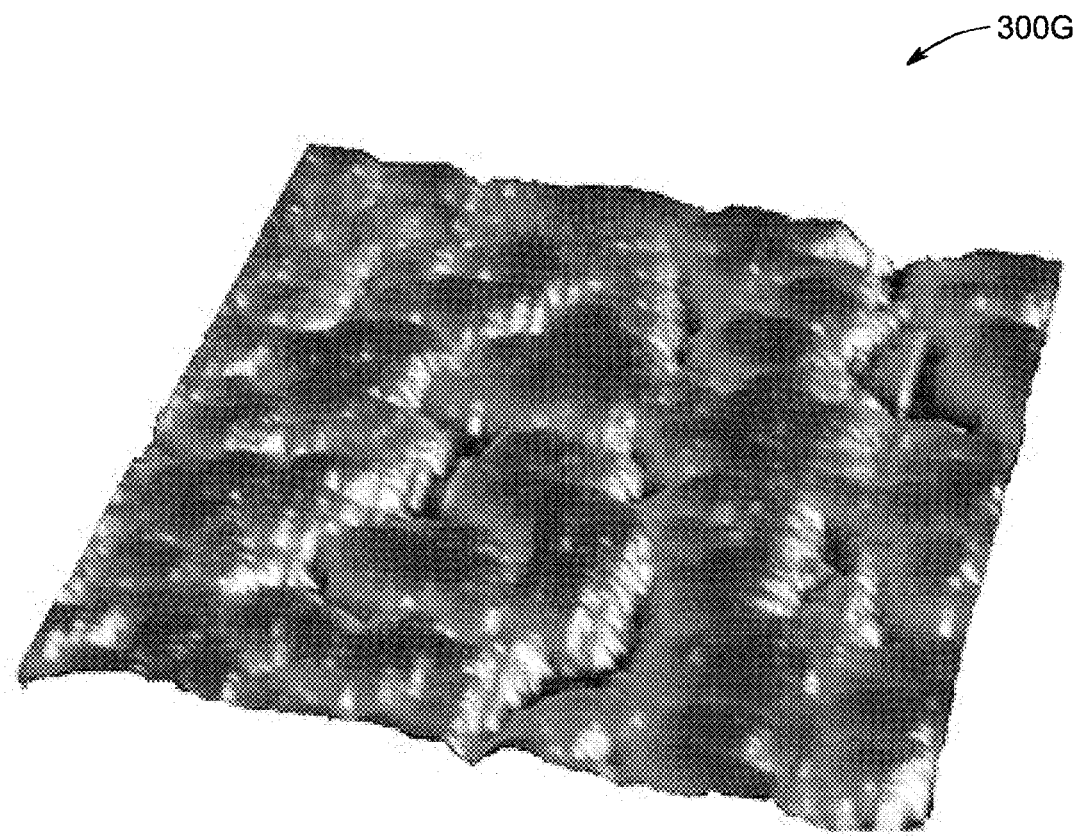
FIG. 3G is a 3D mapping image of the hydrogen gas sensor, according to certain embodiments.

Referring to FIG. 3G, illustrated is a 3D mapping image (as represented by reference numeral 300G) of the hydrogen gas sensor (such as, the hydrogen gas sensor 200F). The 3D mapping image 300G may allow to visualize the hills and the dips (as discussed) in the hydrogen gas sensor 200F in detail. Herein, the 3D mapping image 300G is captured for a same area of the hydrogen gas sensor 200F as the captured 2D topographic mapping image 300D thereof. In the present examples, the 3D mapping image 300G may be rendered by using readings from the same surface profilometer, as implemented for capturing the 2D topographic mapping image 300D. As may be contemplated by a person skilled in the art, the 3D mapping image 300G provides islands-like view (along with the abovementioned height profiles) which confirms the hills and the dips, and indicates that the surface topography of the hydrogen gas sensor 200F is indeed constituted of microscopic structures.

Figure 4A:
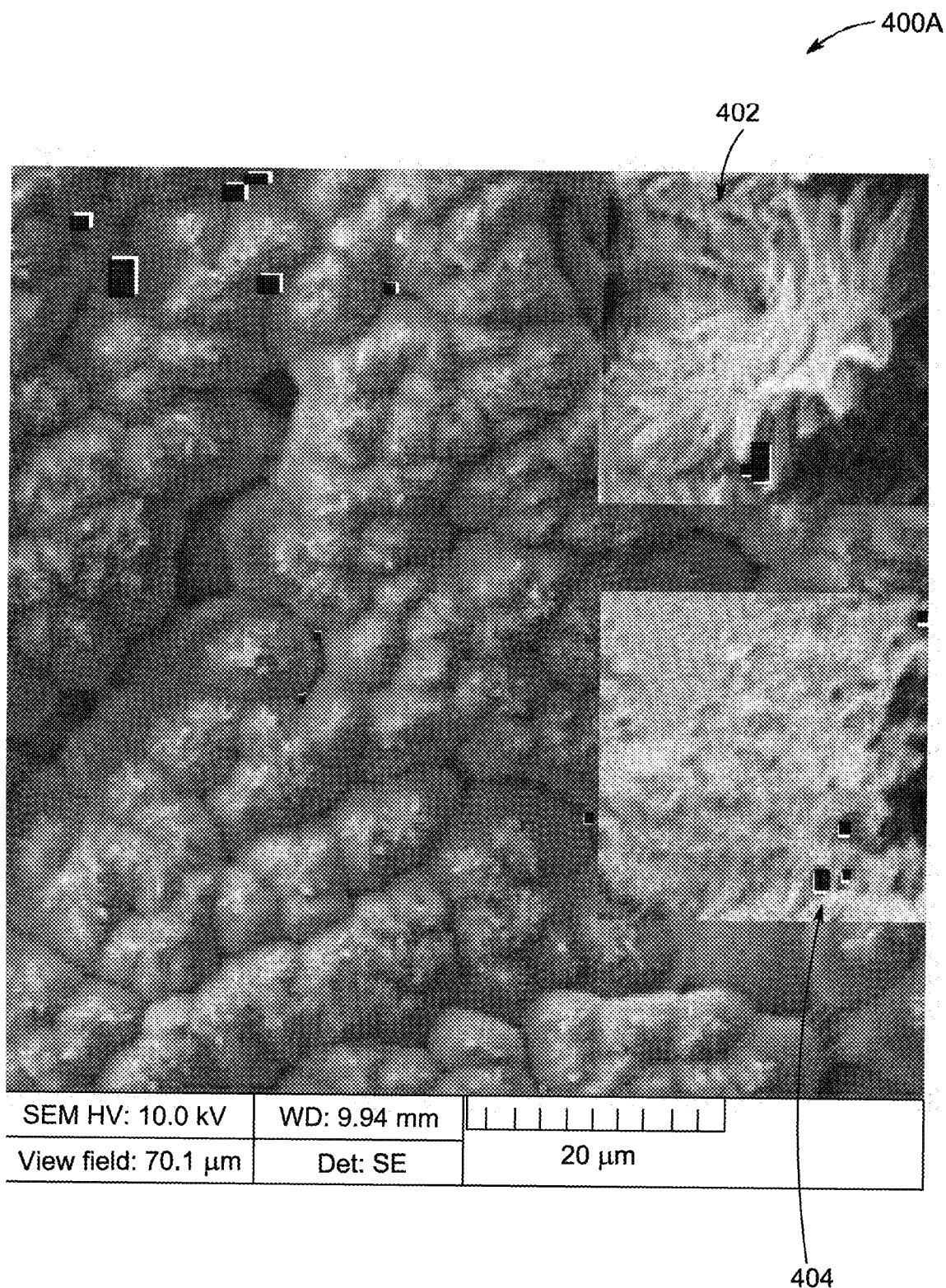
FIG. 4A is a Field Emission Scanning Electron Microscope (FESEM) micrograph image of the hydrogen gas sensor, according to certain embodiments.

Referring now to FIG. 4A, illustrated is a Field Emission Scanning Electron Microscope (FESEM) micrograph image (as represented by reference numeral 400A) of the hydrogen gas sensor (such as, the hydrogen gas sensor 200F). The FESEM micrograph image 400A provides topographic confirmation and in-depth morphology of the nanostructure of the hydrogen gas sensor 200F. In particular, the FESEM micrograph image 400A provides details of nanoscale micrographs in the nanostructure of the hydrogen gas sensor 200F, which allows to validate and reconfirm the inherent characteristics of a hydrophobic surface of the hydrogen gas sensor 200F. In an example, the FESEM micrograph image 400A is obtained by using a high-resolution FESEM (such as, Tescan model #LYRA3). Herein, the FESEM micrograph image 400A of FIG. 4A is a low-resolution FESEM micrograph which confirms fine nanostructures on the top of base nanostructures, in the hydrogen gas sensor 200F.

Figure 4B:
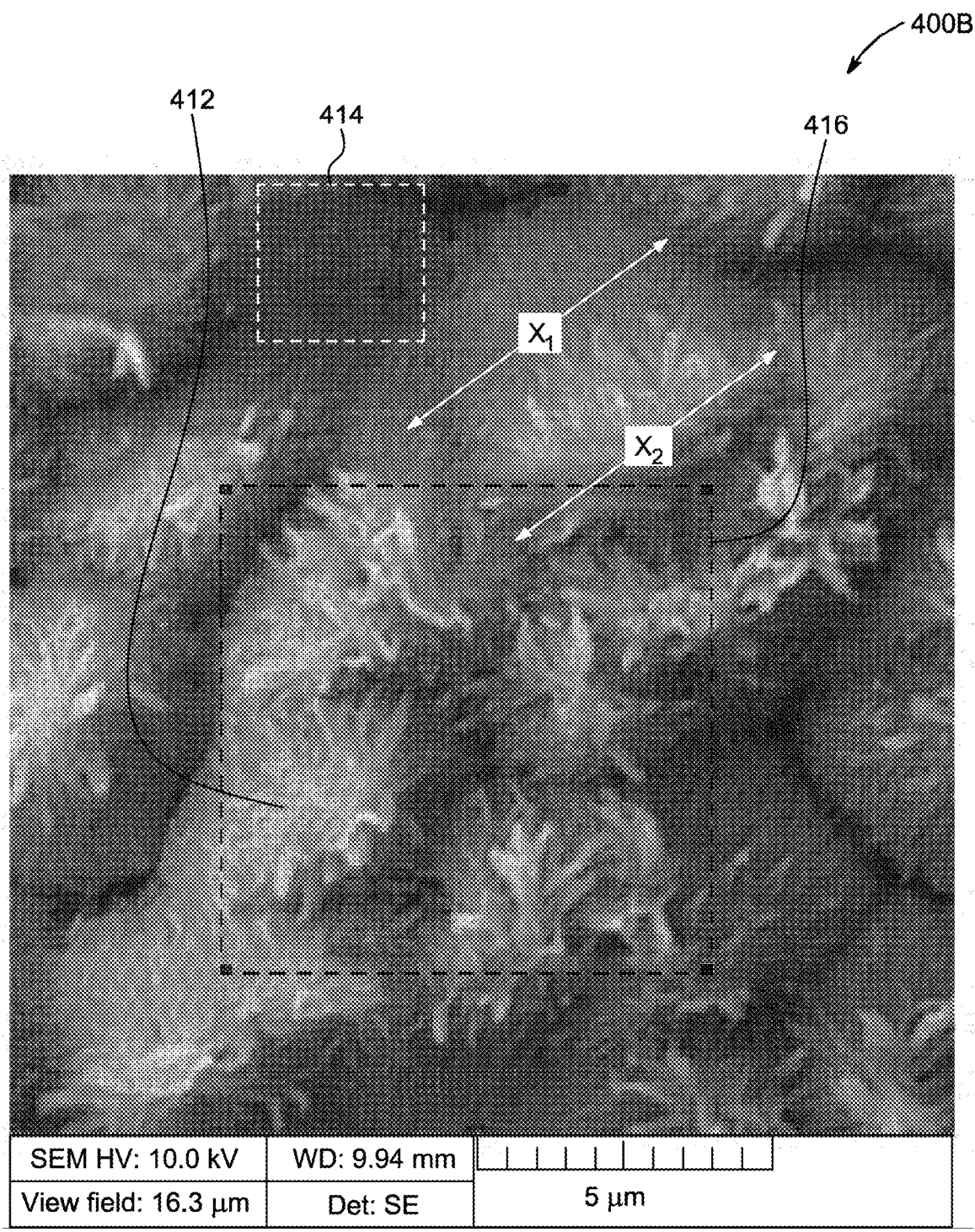
FIG. 4B is a high-resolution FESEM micrograph image of the hydrogen gas sensor, according to certain embodiments.

Referring to FIG. 4B, illustrated is a high-resolution FESEM micrograph image (as represented by reference numeral 400B) of the hydrogen gas sensor (such as, the hydrogen gas sensor 200F). The high-resolution FESEM micrograph image 400B of FIG. 4B reveals that the fine nanostructures on the top of base nanostructure are indeed similar to nanoflowers, which consists of petals of different sizes and shapes. A zoomed-in view of an individual nanoflower (as represented by reference numeral 412 in FIG. 4B) is shown as an inset 402 in FIG. 4A. Also, a zoomed-in view of the base nanostructure (shown as dashed white rectangle and represented by reference numeral 414 in FIG. 4B) is shown as an inset 404 in FIG. 4A.

Figure 4C:
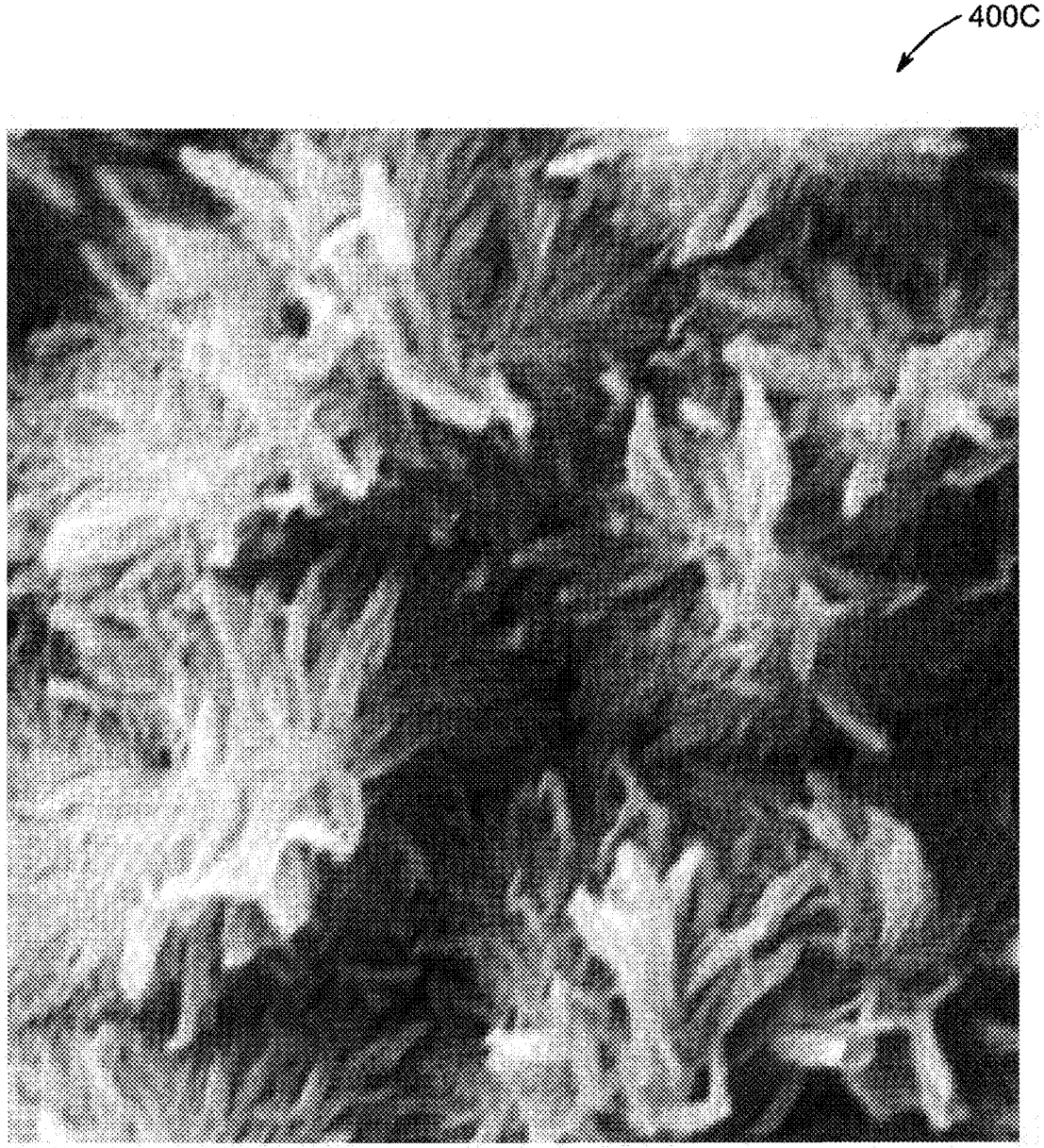
FIG. 4C is a zoomed-in view of a portion from the high-resolution FESEM micrograph image of FIG. 4B, according to certain embodiments.
Figure 4D:
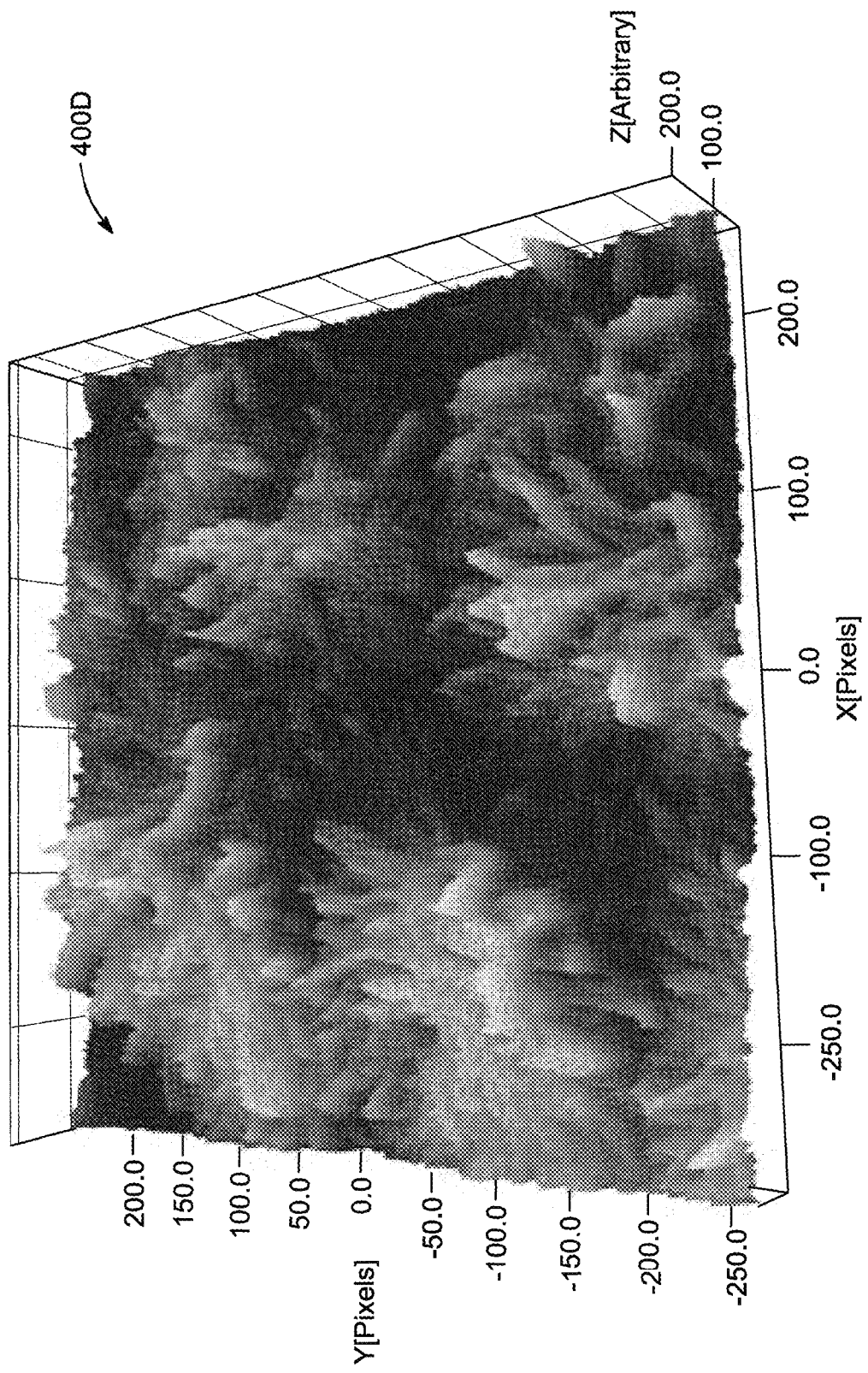
FIG. 4D is a 3D hawk-eye view of the said portion from the high-resolution FESEM micrograph image of FIG. 4B, according to certain embodiments.

Further, FIG. 4C illustrates a zoomed-in view (as represented by reference numeral 400C) of a portion 416 (as represented by dashed black rectangle) from the high-resolution FESEM micrograph image 400B of FIG. 4B. As may be seen from FIG. 4C, a number of nanoflowers (seven, in particular) of different sizes have been observed on top of base nanostructures. Furthermore, FIG. 4D illustrates a 3D hawk-eye view (as represented by reference numeral 400D) of the said portion 416 from the high-resolution FESEM micrograph image 400B of FIG. 4B. As may be observed from the 3D hawk-eye view 400D of FIG. 4D, the nanoflowers are located on the top of base nanostructures. As a result, it may be concluded that the hydrogen gas sensor 200F includes two different layers of nanostructures, one at the base and the other at the top, i.e., the hydrophobic nanostructures and the nanoflowers, respectively. Herein, as may be contemplated by a person skilled in the art, the combination of these two nanostructure layers makes the ultimate surface of the hydrogen gas sensor 200F as highly hydrophobic.

Figure 4E:
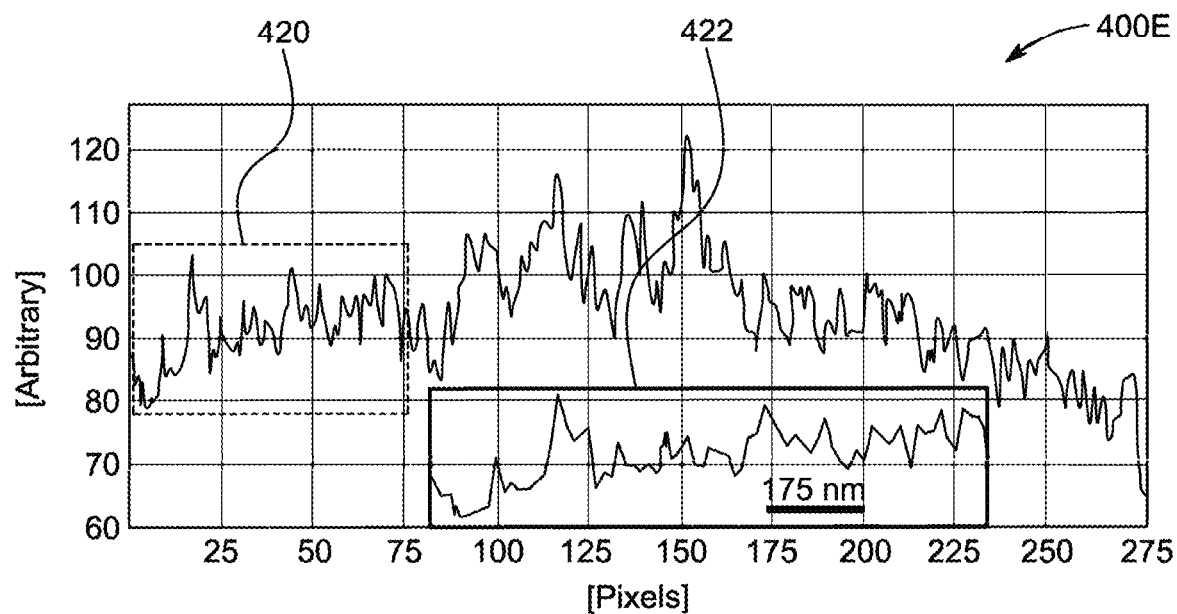
FIG. 4E is a graph representing long-range line scans of the high-resolution FESEM micrograph image of FIG. 4B along a first axis defined therein, according to certain embodiments.
Figure 4F:
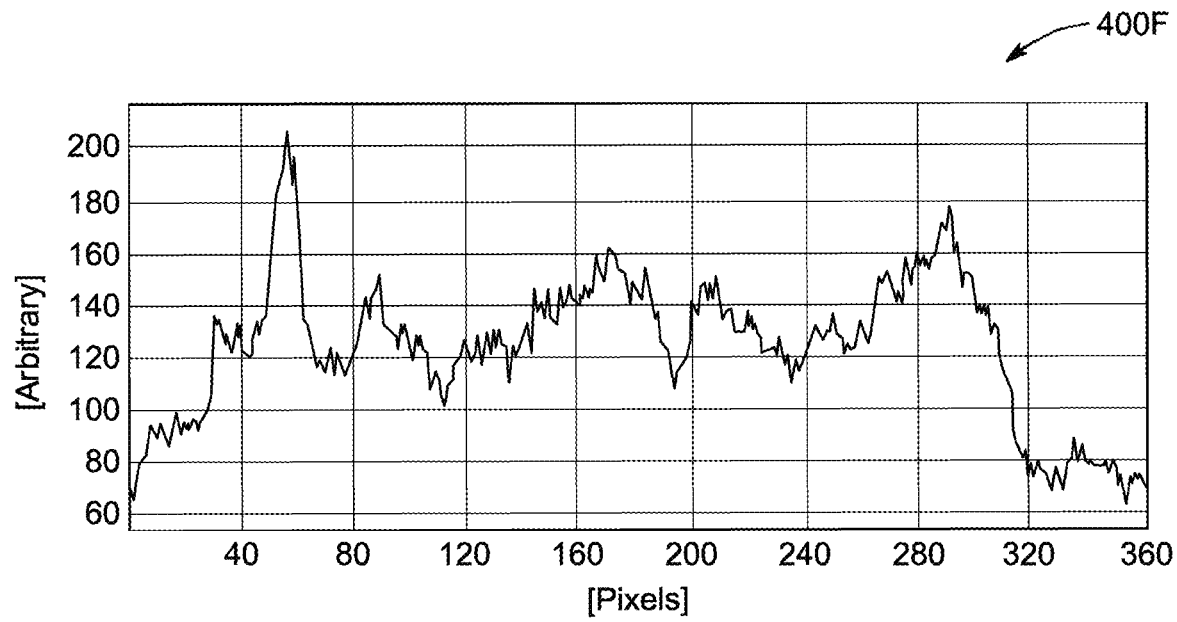
FIG. 4F is a graph representing long-range line scans of the high-resolution FESEM micrograph image of FIG. 4B along a second axis defined therein, according to certain embodiments.

Referring to FIG. 4E, illustrated is a graph representing a long-range line scan 400E along a first axis (represented as '$X_1$' in FIG. 4B) disposed across the base nanostructure in the high-resolution FESEM micrograph image 400B of FIG. 4B. Further, a zoomed-in view of a small section of the long-range line scan 400E (as represented by dashed rectangle 420 in FIG. 4E) is shown as an inset 422 in FIG. 4E itself. Referring to FIG. 4F, illustrated is a graph representing a long-range line scan 400F along a second axis (represented as '$X_2$' in FIG. 4B) disposed across the nanoflower structure in the high-resolution FESEM micrograph image 400B of FIG. 4B. As may be observed, sharp hills in the long-range line scan 400F of FIG. 4F correspond to the petals of the nanoflowers. In other words, in the present embodiments, the nanoscale petals are arranged in the form of microscopic flowers. Herein, the microscopic flowers are on a surface. In an embodiment, the nanoscale petals have an average length in a range of 0.5 to 15 μm, preferably to 12 μm, preferably 1 to 10 μm with an average width in a range of 50 to 1000 nm, preferably to 900 nm, preferably 100 to 800 nm. Specifically, in the present embodiments, the nanoscale petals have an average length in a range of 0.5 to 5 μm, preferably 1 to 4 μm, preferably 1 to 3 μm, preferably 1 to 2.5 μm with an average width in a range of 100 to 500 nm, preferably 125 to 480 nm, preferably 150 to 450 nm. Thus, it may be appreciated that the hydrophobic nanostructures and the palladium layer form a double-layer structure. It may be contemplated by a person skilled in the art that such double layers nanostructure may provide enough void to satisfy Cassie and Baxter state, and facilitate hydrophobicity as required by the hydrogen gas sensor 200F.

Now, it is well-acknowledged that wetting contact angle (WCA) is a measure of indication whether the surface is hydrophobic or hydrophilic. Traditionally, sessile drop test is used to measure the WCA directly, and further determine preferential wetting of a substrate by reference liquid. In the present embodiments, the sessile drop test is carried out to estimate hydrophobicity of the hydrogen gas sensor (such as, the hydrogen gas sensor 200F). Herein, deionized (DI) water may be used as reference liquid. Further, a volume of the water droplet (droplet volume) may be controlled by using an automatic dispensing system (as known in the art and thus not described herein). In an example, the WCA measurements may be carried out using a goniometer (such as Kyowa model #DM 501) for the sessile drop tests. Further, water droplet images of the water droplets are taken one second after deposition of the water droplet on a given surface.

Figure 5A:
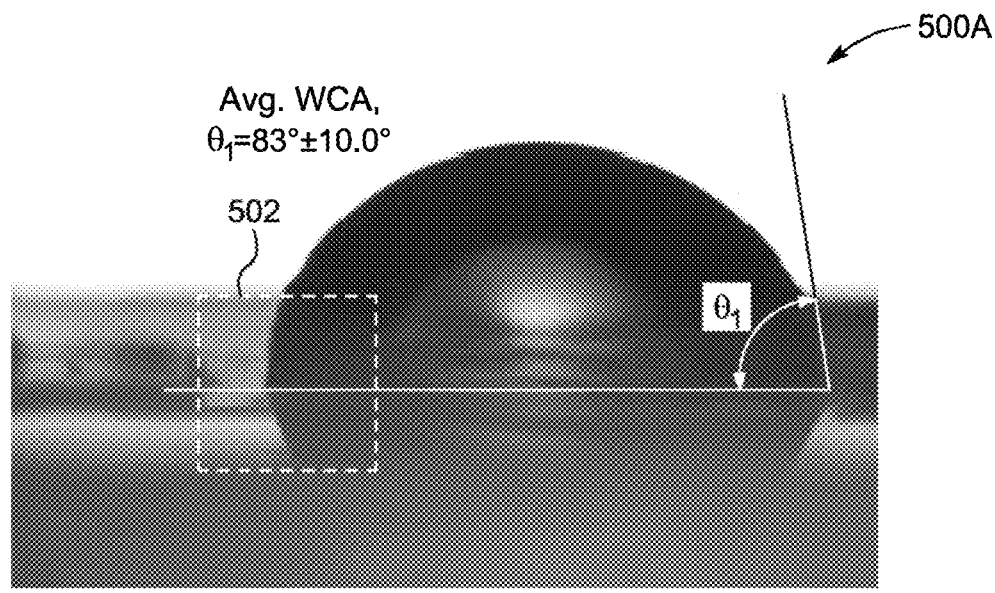
FIG. 5A is a water droplet image showing a wetting contact angle for the pristine polycarbonate sample of FIG. 2B, according to certain embodiments.
Figure 5B:
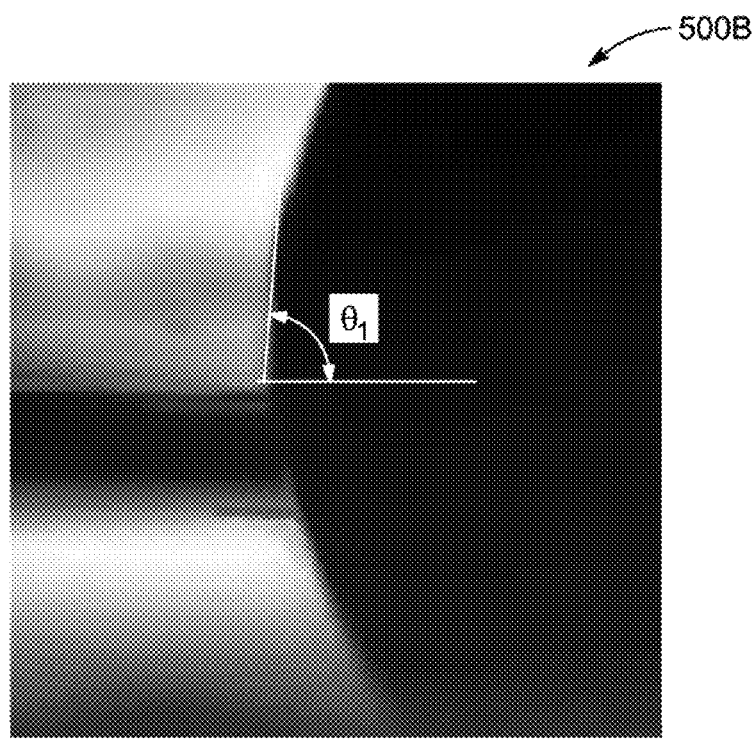
FIG. 5B is a zoomed-in view of a contact region of the water droplet image of FIG. 5A, according to certain embodiments.

FIG. 5A is a water droplet image (as represented by reference numeral 500A) showing a WCA (represented as '$\theta_1$') for the pristine polycarbonate sample 200B of FIG. 2B. Herein, an average WCA '$\theta_1$' for the pristine polycarbonate sample 200B is estimated to be 70°±30.0°, preferably 70°±28.0°, preferably 83°±10.0°. Further, FIG. 5B illustrates a zoomed-in view (as represented by reference numeral 500B) of a contact region (shown as white dashed rectangle and represented by reference numeral 502 in FIG. 5A) of the water droplet image 500A of FIG. 5A. A lower part of the zoomed-in view 500B of FIG. 5B represents a mirror region of the water droplet on the pristine polycarbonate sample 200B, which may be visibly clear enough as the pristine polycarbonate sample 200B is noted to be highly transparent.

Figure 5C:
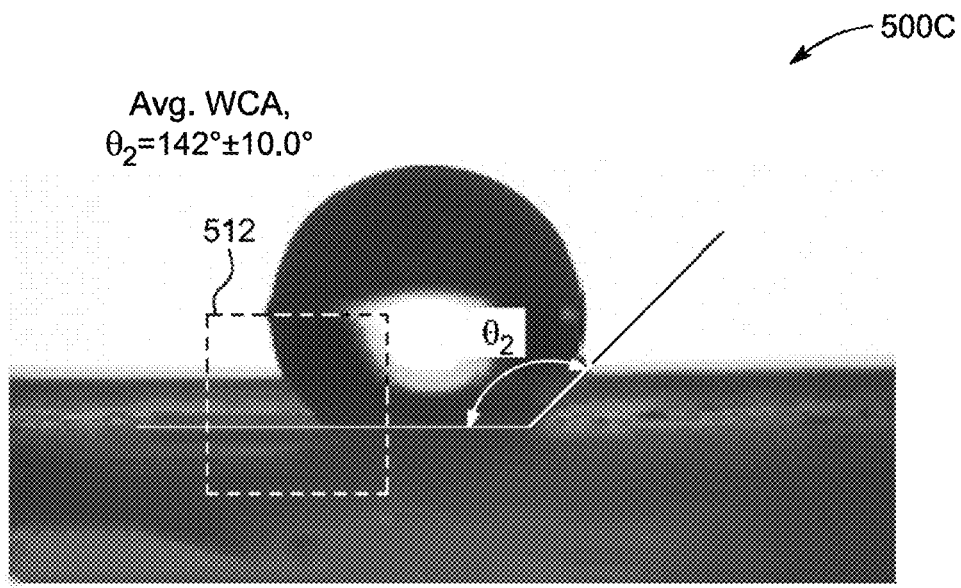
FIG. 5C is a water droplet image showing a wetting contact angle for the treated polycarbonate sample of FIG. 2D, according to certain embodiments.
Figure 5D:
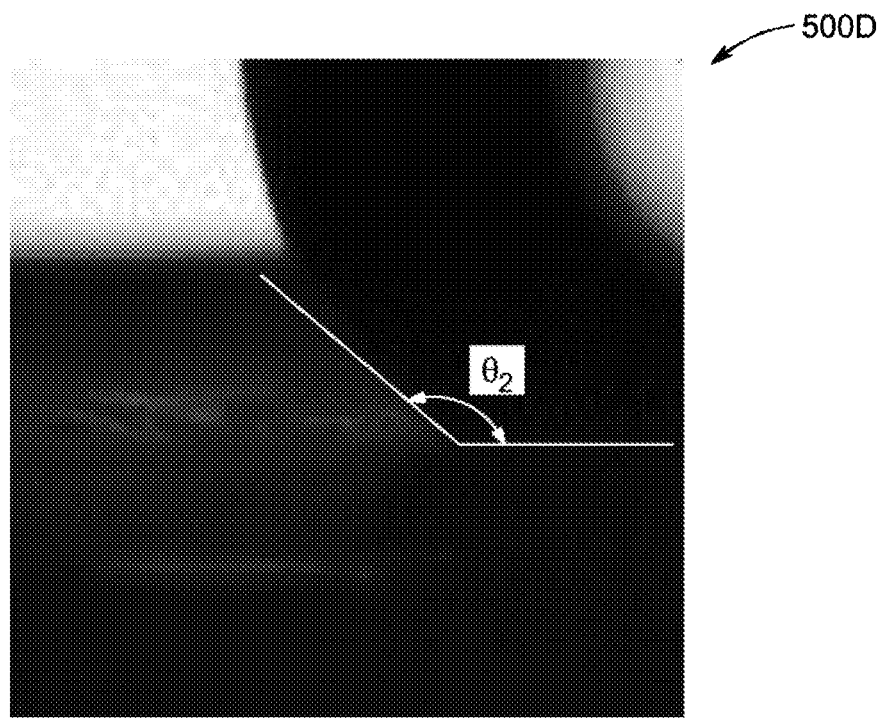
FIG. 5D is a zoomed-in view of a contact region of the water droplet image of FIG. 5C, according to certain embodiments.

FIG. 5C is a water droplet image (as represented by reference numeral 500C) showing a WCA (represented as '$\theta_2$') for the treated polycarbonate sample 200D of FIG. 2D. As may be understood that the treated polycarbonate sample 200D is formed once the pristine polycarbonate sample 200B is treated. Herein, the sessile drop test confirms that the WCA '$\theta_2$' of the treated polycarbonate sample 200D to be as high as ~140°±30.0°, preferably ~140°±25.0°, preferably ~142°±10.0°. As explained earlier, the high-resolution FESEM micrograph image 400B revealed a double layer of nanostructures with fine nanoflower-like structures observed on the top of the base nanostructures. Such a combination of nanostructures may facilitate enough voids to yield the top surface to be highly hydrophobic, and thus the high WCA '$\theta_2$'. Further, FIG. 5D illustrates a zoomed-in view (as represented by reference numeral 500D) of a contact region (shown as white dashed rectangle and represented by reference numeral 512 in FIG. 5C) of the water droplet image 500C of FIG. 5C. A lower part of the zoomed-in view 500D of FIG. 5D represents a mirror region of the water droplet on the treated polycarbonate sample 200D which may be blurred as the transparency of the treated polycarbonate sample 200D dropped substantially post treatment (as discussed).

Figure 5E:
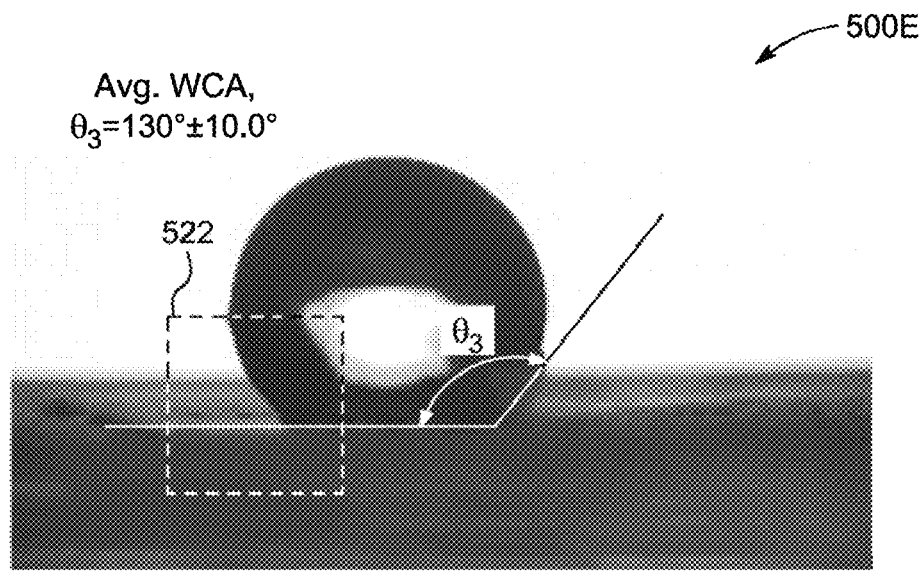
FIG. 5E is a water droplet image showing a wetting contact angle for the Palladium-decorated polycarbonate substrate of FIG. 2F, according to certain embodiments.
Figure 5F:
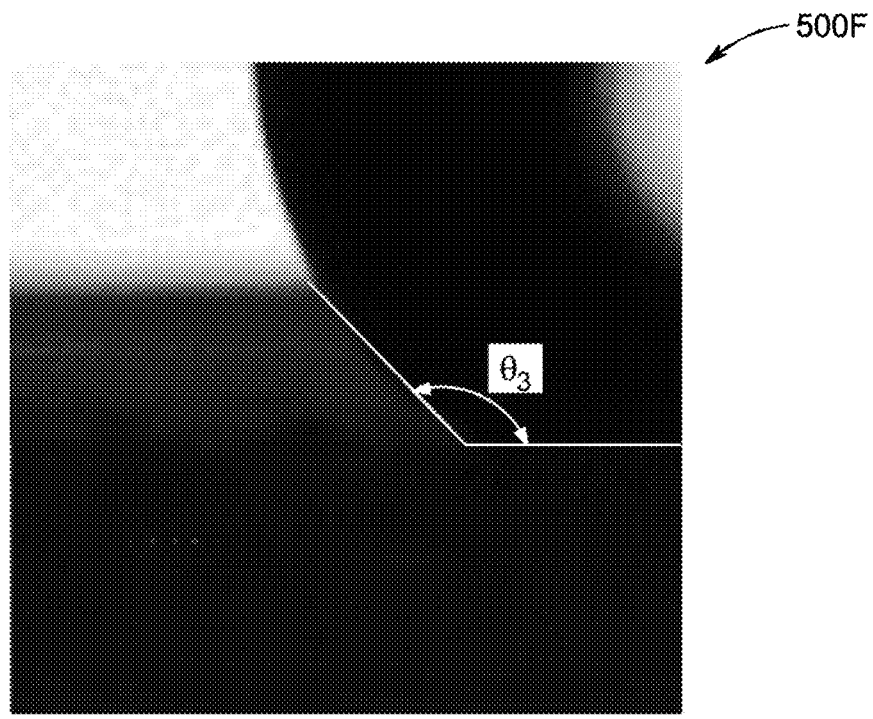
FIG. 5F is a zoomed-in view of a contact region of the water droplet image of FIG. 5E, according to certain embodiments.

FIG. 5E is a water droplet image (as represented by reference numeral 500E) showing a WCA (represented as '$\theta_3$') for the Pd-decorated polycarbonate substrate 200F of FIG. 2F. In the present embodiments, the polycarbonate substrate 200F has the wetting contact angle '$\theta_3$' in a range of 100° to 180.0°, preferably 105° to 175°, preferably 110.0° to 170.0°, preferably 112.0° to 162.0°. Herein, an average WCA '$\theta_3$' for the Pd-decorated polycarbonate substrate 200F is estimated to be 110°±40.0°, preferably 120°±20.0°, preferably 130°±10.0°. As may be observed, the WCA '$\theta_3$' for the Pd-decorated polycarbonate substrate 200F may be a bit lower than that observed for the treated polycarbonate sample 200D. That said, the WCA '$\theta_3$' for the Pd-decorated polycarbonate substrate 200F may still be higher compared to that observed for the pristine polycarbonate sample 200B, and thus may be sufficient enough for hydrogen gas ($H_2$) sensing applications as expected from the hydrogen gas sensor 200F of the present disclosure. Further, FIG. 5F illustrates a zoomed-in view (as represented by reference numeral 500F) of a contact region (shown as white dashed rectangle and represented by reference numeral 522 in FIG. 5E) of the water droplet image 500E of FIG. 5E. A lower part of the zoomed-in view 500F of FIG. 5F represents a mirror region of the water droplet on the Pd-decorated polycarbonate substrate 200F, which may again be blurred as the Pd-decorated polycarbonate substrate 200F is formed from the treated polycarbonate sample 200D.

Figure 6:
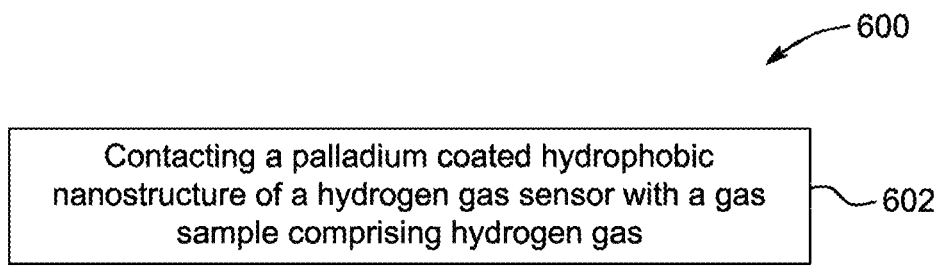
FIG. 6 is a flowchart of a method of using the hydrogen gas sensor, according to certain embodiments.

Referring now to FIG. 6, illustrated is a flowchart of a method (represented by reference numeral 600) of using the hydrogen gas sensor (such as, the hydrogen gas sensor 200F). At step 602 of the method 600, the method 600 includes contacting the palladium coated hydrophobic nanostructure of the hydrogen gas sensor 200F with a gas sample comprising hydrogen gas ($H_2$). In the present embodiments, the gas sample has a temperature of 0 to 80° C., preferably 0 to 70° C., preferably 0 to 60° C., preferably 0 to 50° C. Thus, the present hydrogen gas sensor 200F is designed to be capable to sense the hydrogen gas ($H_2$) within the said temperature range. Generally, for most applications, the gas sample is 20 to 30° C. Further, the hydrogen gas sensor 200F for implementation of the present method 600 has a repeatability of at least 80 to 99%, preferably 85 to 99%, preferably 90 to 99%, preferably 95 to 99%, preferably 99%. That is, the hydrogen gas sensor 200F may provide accurate sensing of the hydrogen gas ($H_2$) for at least 80 to 99%, preferably 85 to 99%, preferably 90 to 99%, preferably 95 to 99%, preferably 99% of the various tested gas samples.

Figure 7:
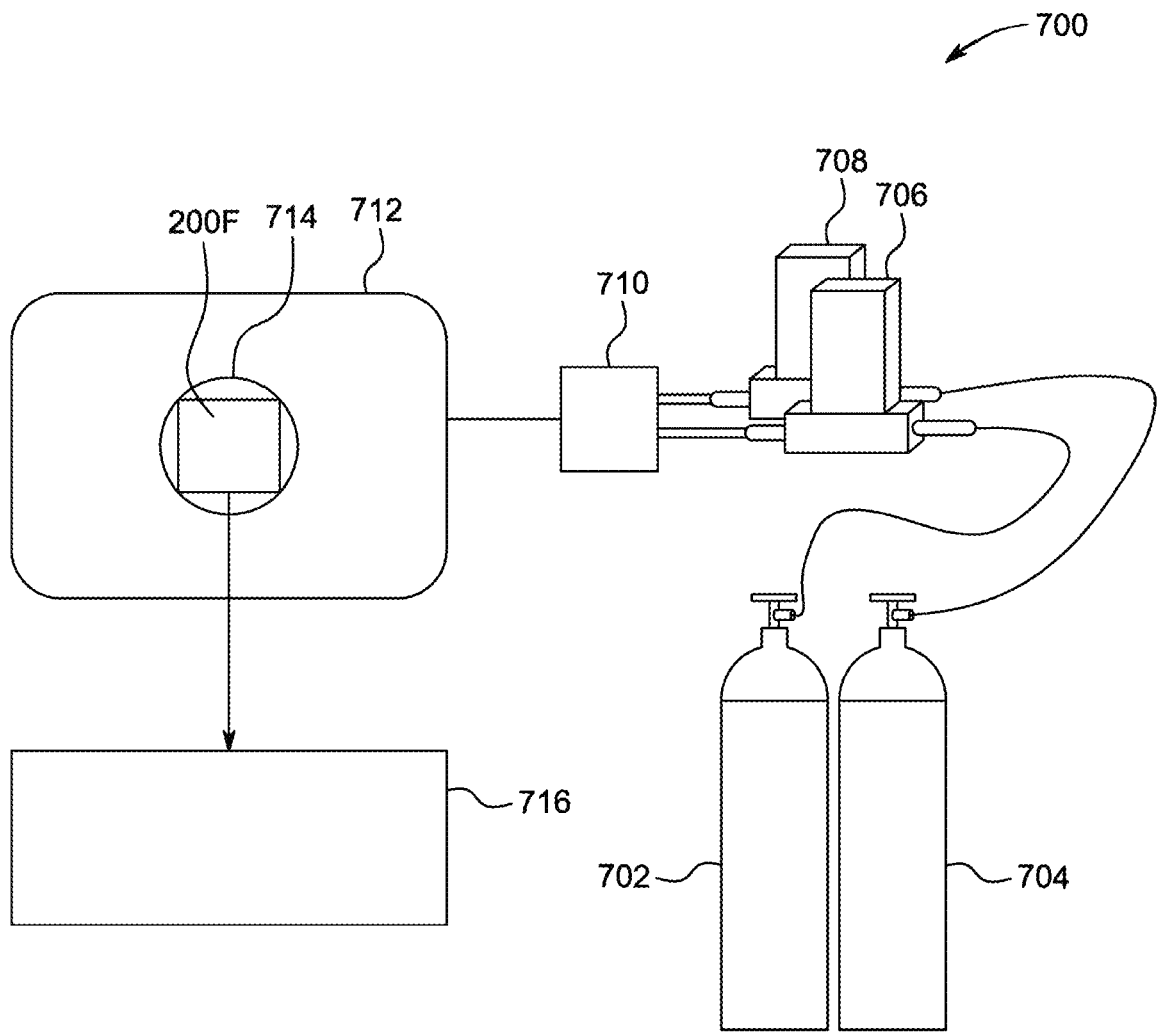
FIG. 7 is a schematic of a sensing arrangement for testing sensing characteristics of the hydrogen gas sensor, according to certain embodiments.

Referring to FIG. 7, illustrated is a schematic of a sensing arrangement 700 for testing sensing performance of the hydrogen gas sensor 200F. As shown, the sensing arrangement 700 includes a hydrogen gas ($H_2$) cylinder 702 containing pressurized hydrogen gas and a nitrogen gas ($N_2$) cylinder 702 containing pressurized nitrogen gas. The sensing arrangement 700 further includes a first mass flow controller 706 connected to the hydrogen gas cylinder 702 and a second mass flow controller 708 connected to the nitrogen gas cylinder 704. The mass flow controllers 706 and 708, respectively, control flow of the hydrogen gas from the connected hydrogen gas cylinder 702 and the nitrogen gas from the connected nitrogen gas cylinder 704, such that a gaseous mixture containing 0.5 to 10%, preferably 0.5 to 4%, preferably 0.5 to 3%, preferably 0.5 to 2%, preferably 1% $H_2$ and 90 to 99%, preferably 95 to 99%, preferably 96 to 99%, preferably 97 to 99%, preferably 99% $N_2$ is obtained in a gas mixing chamber 710 of the sensing arrangement 700. Herein, in an example, the mass flow controllers 706, 708 may utilize an external power hub supply (such as, XPH-100) to control the flow of the hydrogen gas and the nitrogen gas, respectively. In the sensing arrangement 700, the said gaseous mixture from the gas mixing chamber 710 is transferred to a gas sensing chamber 712 thereof. In an example, the gas sensing chamber 712 is a customized stage chamber (such as, Linkam Model #HFS-600E-PB4, UK, as known in the art) which incorporates the gaseous mixture sequentially. In the gas sensing chamber 712, the gaseous mixture is kept at room temperature for performing sensing measurements. In some examples, the $H_2$ concentration in the gas sensing chamber 712 may be varied by mixing the gaseous mixture (1% $H_2$ balanced with $N_2$) with dry air. Further, the gas sensing chamber 712 may be connected to a cooling system (generally represented by reference numeral 714) to maintain the gaseous mixture at the room temperature inside thereof. In the gas sensing chamber 712, the gaseous mixture comes in contact with the hydrogen gas sensor 200F, which in turn generate electrical signals indicative of sensed properties thereof. As shown, the sensing arrangement 700 further includes an analyzer 716 (such as, a semiconductor analyzer) coupled to the hydrogen gas sensor 200F in order to convert the electrical signals into comprehensible readings. In an example, the analyzer 716 is an Agilent B1500A Semiconductor Device Analyzer (SDA) as known in the art.

Figure 8A:
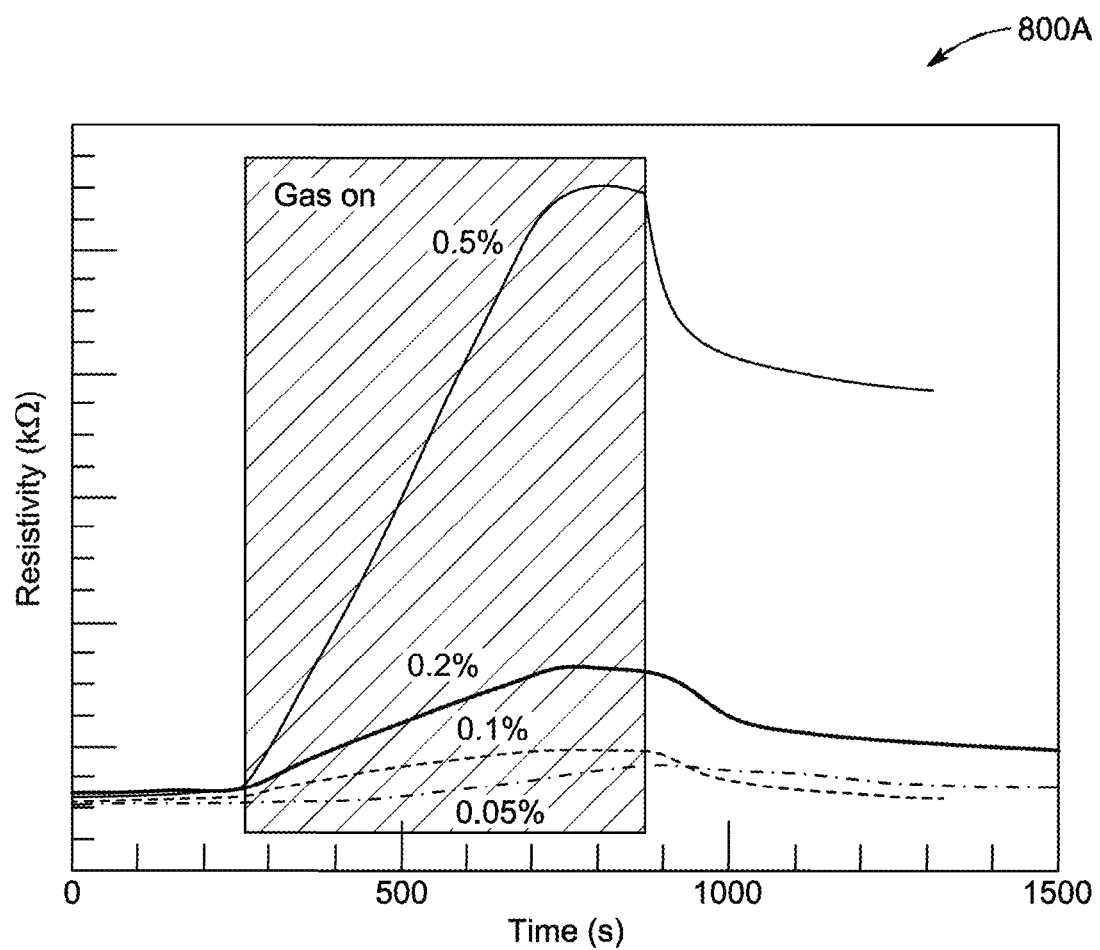
FIG. 8A is a graph showing dynamic response of the hydrogen gas sensor to different hydrogen gas concentrations at room temperature, according to certain embodiments.

FIG. 8A is a graph 800A showing dynamic response of the hydrogen gas sensor 200F to different hydrogen gas concentrations at room temperature. Specifically, the graph 800A shows dynamic responses of the hydrogen gas sensor 200F for $H_2$ gas concentration of 0.05%, 0.1%, and 0.5% at 20 to 30° C. As may be observed from the graph 800A, for intake of low concentration such as 0.05% of $H_2$ concentration, the response (which is indirectly measured from resistivity (in KΩ) reading from the analyzer 716) is delayed and started to show up after 400 to 800 seconds, preferably 500 to 700 seconds, preferably 500 to 600 seconds, preferably 500 seconds; and for cases of other intakes, such as 0.1%, 0.21% and 0.5% of $H_2$ concentrations, the responses starts from 100 to 500 seconds, preferably 200 to 400 seconds, preferably 300 seconds. It may also be observed that response characteristics from each intake of $H_2$ concentrations is different. To understand the varied response characteristics, a gradient (AG) of the response characteristics is calculated by equation:

$$\Delta G = \frac{\partial R}{\partial T}.$$

Using this equation, the rising gradients of the dynamic responses of the hydrogen gas sensor 200F for 0.05%, 0.1%, 0.2%, and 0.5% of $H_2$ concentrations are estimated to be 0.16 (delayed), 0.16, 0.36 and 2.05, respectively.

Figure 8B:
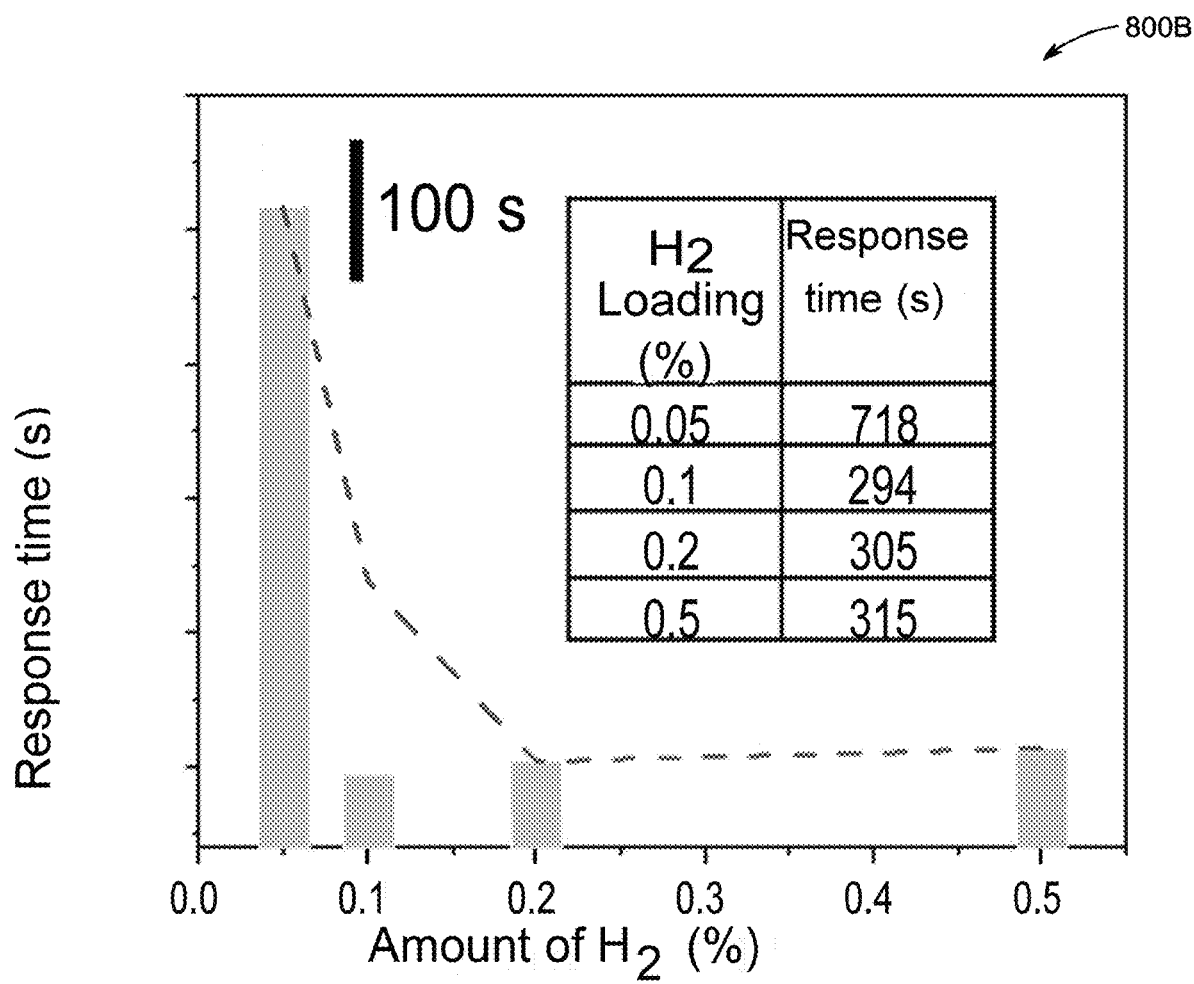
FIG. 8B is a graph showing response time of the hydrogen gas sensor to different hydrogen gas concentrations at room temperature, according to certain embodiments.

FIG. 8B is a graph 800B showing response time of the hydrogen gas sensor 200F to different hydrogen gas concentrations at room temperature. It may be understood that a response time of a gas sensor is one of the crucial parameters that define the speed of response of that particular gas sensor. Traditionally, the response time is measured by the time taken for a sensor to reach 85 to 94%, preferably 87 to 92%, preferably 90% of the final indication of saturation. Table 1 below provides the response times of the hydrogen gas sensor 200F for 0.05%, 0.1%, and 0.5% of $H_2$ concentrations. Herein, for the intake of $H_2$ concentrations of 0.05%, 0.1%, and 0.5%, the hydrogen gas sensor 200F has the response time of 700 to 800 seconds, preferably 718 seconds, 280 to 330 seconds, preferably 294 seconds, 280 to 340 seconds, preferably 305 seconds, and 300 to 330 seconds, preferably 315 seconds, respectively. It may be observed from the graph 800B that the response time of the hydrogen gas sensor 200F is slow at low $H_2$ concentrations, and increases till the response time is almost constant for higher $H_2$ concentrations.

TABLE 1

| Response time of hydrogen gas sensor | |
|---|---|
| $H_2$ Loading (%) | Response Time (s) |
| 0.05 | 718 |
| 0.1 | 294 |
| 0.2 | 3.5 |
| 0.3 | 315 |

Figure 8C:
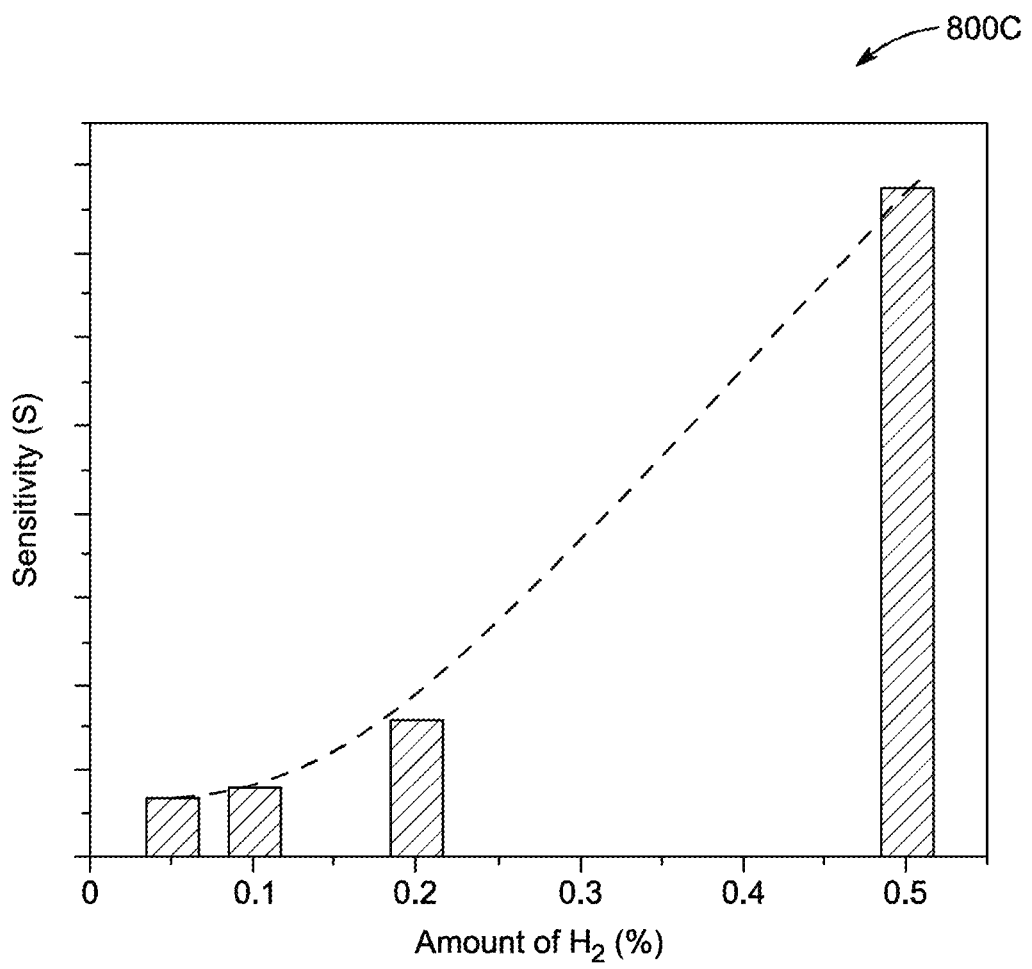
FIG. 8C is a graph showing sensitivity of the hydrogen gas sensor to different hydrogen gas concentrations at room temperature, according to certain embodiments.

FIG. 8C is a graph 800C showing sensitivity of the hydrogen gas sensor 200F to different hydrogen gas concentrations at room temperature. It may be understood that sensitivity is another crucial characteristic that indicates how efficiently the target gas can be detected by a given sensor. The sensitivity of a gas sensor is given by equation, $$\text{Sensitivity (\%)} = \frac{R_g - R_a}{R_a},$$

where $R_a$ and $R_g$ are resistances of the sensor in air and target gas, respectively. Table 2 below provides the sensitivity of the hydrogen gas sensor 200F for 0.05%, 0.1%, 0.2%, and 0.5% of $H_2$ concentrations. Herein, for the intake of $H_2$ concentrations of 0.05%, 0.1%, 0.2%, and 0.5%, the hydrogen gas sensor 200F has the sensitivity of 5 to 8%, preferably 7%, 6 to 9%, preferably 8%, 15 to 18%, preferably 16%, and 75 to 80%, preferably 77%, respectively. It may be observed from the graph 800C that the sensitivity (which is indirectly measured from electrical resistance reading from the analyzer 716) increases with increase in the $H_2$ concentration.

TABLE 2

Sensitivity of hydrogen gas sensor

| $H_2$ Loading (%) | Sensitivity (%) |
|---|---|
| 0.05 | 7 |
| 0.1 | 8 |
| 0.2 | 16 |
| 0.3 | 77 |

Thereby, the present disclosure provides a simple process to fabricate the hydrogen gas sensor 200F having polymer-templated hydrophobic nanostructures as hydrogen gas sensing platforms. Preliminary topographic investigations through the 3D optical microscope and the surface profilometer indicates irregular hills and dips of various dimensions that would be responsible to create air-bubble pockets to satisfy Cassie-Baxter state of hydrophobicity for the hydrogen gas sensor 200F. Further, an in-depth surface topography investigation by high-resolution FESEM provides that fine microscopic flower-like structures of nanoscale petals are populated on the top of base nanostructures. Such nano-flowers decorated with Pd sensing materials exhibited relatively high WCA and facilitated high surface area to adsorb target gas simultaneously. In particular, high-resolution field-emission scanning electron microscopy (FESEM) reveals double-layer structures for the hydrogen gas sensor 200F consisting of fine microscopic flower-like structures of nanoscale petals on the top of base nanostructures. Herein, the double layer micro-structures and nano-structures of the hydrogen gas sensor 200F plays a vital role to satisfy Cassie-Baxter state and yielded hydrophobic surface. Wetting contact angle (WCA) measurements for the base nanostructure of hydrogen gas sensor 200F reveals the wetting contact angle to be ~120.0°±40.0°, preferably ~125.0°±30.0°, preferably ~130.0°±25.0°, preferably ~140.0°±15.0°, preferably ~142.0°±10.0°. From this direction, the hydrogen gas sensor 200F has a very thin layer of palladium (ca. 80 to 120 nm, preferably 90 to 110 nm, preferably 100 nm of thickness) sputtered therein. FESEM micrographs for the fully formed hydrogen gas sensor 200F reveals that microscopic flower-like structures of nanoscale petals remain intact. Further, sessile drop test reconfirms the WCA to be as high as ~110.0°±40.0°, preferably ~120.0°±30.0°, preferably ~120.0°±20.0°, preferably ~130.0°±10.0°.

Such hydrophobic nanostructures are expected to provide a platform for gas sensing materials of higher surface area. Due to inherent features of hydrophobic nanostructures, the hydrogen gas sensor 200F provides a wider surface area that can be useful for higher target gas adsorption sites. In this context, the customized sensing arrangement 700 is utilized to test for $H_2$ gas sensing performance. It has been found that the surface nanostructures are very stable and durable over the time of a year and beyond. The polymer-based, hydrophobic hydrogen gas sensor 200F as disclosed in the present disclosure plays a dual role in hydrophobicity as well as superior gas sensing characteristics. The proposed simple and inexpensive manufacturing process for the hydrogen gas sensor 200F is indispensable for industrial-scale production line, and to explore new routes of multifunctional sensing platforms, particularly important in extreme environmental conditions.

The invention claimed is:

1. A hydrogen gas sensor, comprising:
   a polycarbonate substrate having hydrophobic nanostructures; and
   a palladium layer in the form of nanoscale petals on the hydrophobic nanostructures.

2. The hydrogen gas sensor of claim 1, wherein the hydrophobic nanostructures have a maximum step height along a horizontal line scan in a range of 3 to 17 µm determined by 2D topographic mapping.

3. The hydrogen gas sensor of claim 1, wherein the hydrophobic nanostructures have a minimum step height along a horizontal line scan in a range of −28 to −14 µm determined by 2D topographic mapping.

4. The hydrogen gas sensor of claim 1, wherein the hydrophobic nanostructures have hills in a line scan along a vertical axis in a range of 6 to 20 µm determined by 2D topographic mapping.

5. The hydrogen gas sensor of claim 1, wherein the hydrophobic nanostructures have dips in a line scan along a vertical axis in a range of −30 to −13 µm determined by 2D topographic mapping.

6. The hydrogen gas sensor of claim 1, wherein the polycarbonate substrate has a wetting contact angle in a range of 112.0° to 162.0°.

7. The hydrogen gas sensor of claim 1, wherein the hydrophobic nanostructures and the palladium layer form a double-layer structure.

8. The hydrogen gas sensor of claim 1, wherein the nanoscale petals are arranged in the form of microscopic flowers.

9. The hydrogen gas sensor of claim 8, wherein the microscopic flowers are on a surface of the hydrophobic nanostructures.

10. The hydrogen gas sensor of claim 8, wherein the nanoscale petals have an average length in a range of 1 to 10 µm with an average width in a range of 100 to 800 nm.

11. The hydrogen gas sensor of claim 10, wherein the nanoscale petals have an average length in a range of 1 to 2.5 µm with an average width in a range of 150 to 450 nm.

12. A method of making the hydrogen gas sensor of claim 1, comprising:
    fabricating the polycarbonate substrate with the hydrophobic nanostructures; and
    coating the polycarbonate substrate with the palladium layer.

13. The method of making the hydrogen gas sensor of claim 12, wherein the polycarbonate substrate is fabricated with a wet chemical treatment.

14. The method of making the hydrogen gas sensor of claim 12, wherein the palladium layer is coated onto the substrate with a sputtering technique.

15. A method of using the hydrogen gas sensor of claim 1, comprising:
   contacting the hydrogen gas sensor with a gas sample comprising hydrogen gas.

16. The method of using the hydrogen gas sensor of claim 15, wherein the gas sample has a temperature of 0 to 50° C.

17. The method of using the hydrogen gas sensor of claim 15, which has a repeatability of at least 99%.

* * * * *